United States Patent [19]

Yoshioka et al.

[11] Patent Number: 4,691,027
[45] Date of Patent: Sep. 1, 1987

[54] 1,3-BENZOXATHIOLE DERIVATIVES

[75] Inventors: Takao Yoshioka; Eiichi Kitazawa; Mitsuo Yamazaki; Yoshio Iizuka, all of Tokyo, Japan

[73] Assignee: Sankyo Company, Limited, Tokyo, Japan

[21] Appl. No.: 716,171

[22] Filed: Mar. 26, 1985

[30] Foreign Application Priority Data

Mar. 28, 1984 [JP] Japan .................................. 59-60198

[51] Int. Cl.$^4$ .................. C07D 327/04; C07D 497/00; A61K 31/39
[52] U.S. Cl. ........................................ 549/32; 549/33; 514/439
[58] Field of Search ............................ 549/23, 32, 33; 514/432, 439

[56] References Cited

FOREIGN PATENT DOCUMENTS 1259054  1/1972  United Kingdom .................. 549/32

OTHER PUBLICATIONS

Taylor et al, Textbook "Introductory Medicinal Chemistry" John Wiley and Sons, 1981 N.Y., pp. 112–113.
Schueler, "Molecular Modification in Drug Design", Am. Chem. Soc., 1964 Wash. D.C. 1964 pp. 140–147.

Primary Examiner—Henry R. Jiles
Assistant Examiner—J. G. Mullins
Attorney, Agent, or Firm—Frishauf, Holtz, Goodman & Woodward

[57] ABSTRACT

Compounds formula (I):

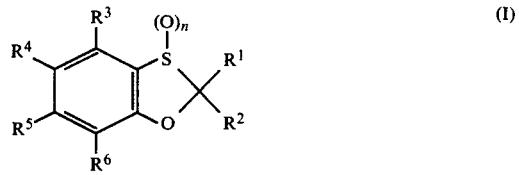

in which: $R^1$ represents a hydrogen atom, an alkyl group, a substituted alkyl group, a $C_2$–$C_6$ alkenyl group, an aryl group, a substituted aryl group or an alkoxycarbonyl group wherein the alkoxy part has from 1 to 6 carbon atoms; $R^2$ represents a hydrogen atom, a $C_1$–$C_6$ alkyl group or a $C_3$ or $C_4$ alkenyl group; $R^3$ represents a hydrogen atom or a $C_1$–$C_6$ alkyl group; $R^4$ represents a hydroxy group, a $C_1$–$C_{21}$ aliphatic acyloxy group or a carbocyclic aryl carboxylic acyloxy group; $R^5$ represents a $C_1$–$C_{12}$ alkyl group, a $C_1$–$C_6$ alkoxy group, a hydroxy group, a $C_1$–$C_7$ aliphatic acyloxy group or a carbocyclic aryl carboxylic acyloxy group; $R^6$ represents a hydrogen atom, a $C_1$–$C_6$ alkyl group or a $C_1$–$C_6$ alkoxy group; and n is 0, 1, or 2; and pharmaceutically acceptable salts thereof are valuable in the treatment of circulatory disorders and allergies.

29 Claims, No Drawings

1,3-BENZOXATHIOLE DERIVATIVES

BACKGROUND TO THE INVENTION

The present invention relates to a series of novel 1,3-benzoxathiole derivatives having a variety of valuable therapeutic activities which make them of value in the treatment of circulatory dysfunctions and of allergies.

The compounds of the present invention have been found to have the ability to lower the level of lipid peroxides in blood, to inhibit the aggregation of blood platelets, to inhibit the formation and release of SRS-A (slow reacting substance of anaphylaxis) and to reduce constriction of air passages, hence leading to their potential use in the treatment of circulatory dysfunctions and allergies. A variety of compounds has been previously described having some or all of these activities [see, for example, C. Malvy et al., Biochemical and Biophysical Research Communications, 95, 734 (1980) and S. Watanabe-Kohno and C. W. Parker, Journal of Immunology, 125, 946 (1980)], but we are unaware of any compounds having a similar activity and structurally related to the compounds of the present invention.

BRIEF SUMMARY OF INVENTION

The compounds of the present invention are those compounds of formula (I):

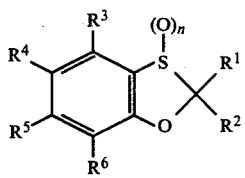

in which:
R$^1$ represents a hydrogen atom, an alkyl group, a substituted alkyl group, a C$_2$–C$_6$ alkenyl group, an aryl group, a substituted aryl group or an alkoxycarbonyl group wherein the alkoxy part has from 1 to 6 carbon atoms, said substituents on said alkyl and aryl groups being selected from the group consisting of: halogen atoms, hydroxy groups, C$_1$–C$_7$ aliphatic acyloxy groups, carbocyclic aryl carboxylic acyloxy groups, α-alkoxyalkoxy groups where both alkoxy parts have from 1 to 6 carbon atoms, oxygen-containing heterocyclyl-oxy groups, trialkylsilyloxy groups where each alkyl part has from 1 to 6 carbon atoms, aralkyloxy groups where the aryl part is C$_6$–C$_{10}$ carbocyclic aryl and the alkyl part is C$_1$–C$_6$ alkyl, C$_1$–C$_6$ alkoxy groups, C$_1$–C$_6$ aminoalkoxy groups, alkylaminoalkoxy groups where the alkyl and alkoxy parts both have from 1 to 6 carbon atoms, dialkylaminoalkoxy groups where the alkyl and alkoxy parts all have from 1 to 6 carbon atoms, carboxy groups, alkoxycarbonyl groups where the alkoxy part has from 1 to 6 carbon atoms, carbamoyl groups, alkylcarbamoyl groups where the alkyl part has from 1 to 6 carbon atoms, dialkylcarbamoyl groups where both alkyl parts have from 1 to 6 carbon atoms and, as substituents on aryl groups only, C$_1$–C$_6$ alkyl groups;

R$^2$ represents a hydrogen atom, a C$_1$–C$_6$ alkyl group or a C$_3$ or C$_4$ alkenyl group;

R$^3$ represents a hydrogen atom or a C$_1$–C$_6$ alkyl group;

R$^4$ represents a hydroxy group, a C$_1$–C$_{21}$ aliphatic acyloxy group or a carbocyclic aryl carboxylic acyloxy group;

R$^5$ represents a C$_1$–C$_{12}$ alkyl group, a C$_1$–C$_6$ alkoxy group, a hydroxy group, a C$_1$–C$_7$ aliphatic acyloxy group or a carbocyclic aryl carboxylic acyloxy group;

R$^6$ represents a hydrogen atom, a C$_1$–C$_6$ alkyl group or a C$_1$–C$_6$ alkoxy group; and n is 0, 1, or 2;

and pharmaceutically acceptable salts thereof.

The invention also provides a composition for the treatment of circulatory disorders and allergies comprising an effective amount of a therapeutic agent in admixture with a pharmaceutically acceptable carrier or diluent, wherein the therapeutic agent is selected from the group consisting of compounds of formula (I) and pharmaceutically acceptable salts thereof.

The invention still further provides a method of treating a mammal suffering from a circulatory disorder or allergy by the administration thereto of an effective amount of a therapeutic agent, wherein the therapeutic agent is selected from the group consisting of compounds of formula (I) and pharmaceutically acceptable salts thereof.

The invention also provides processes for preparing the compounds of the invention, as described in more detail hereafter.

DETAILED DESCRIPTION OF INVENTION

The compounds of the invention are 1,3-benzoxathiole derivatives having the following formula (I) whereon for the avoidance of doubt is indicated the numbering system applied herein:

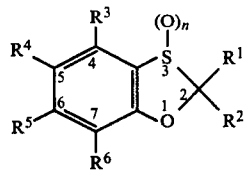

In the compounds of the invention, R$^1$ can represent a hydrogen atom, an optionally substituted alkyl group, a C$_2$–C$_6$ alkenyl group, an optionally substituted aryl group or an alkoxycarbonyl group in which the alkoxy part has from 1 to 6 carbon atoms.

Where R$^1$ represents an optionally substituted alkyl group, this may be a straight or branched chain group, whose length is only restricted by the practical considerations of availability and ease of manipulation. In practice, this means that we generally prefer that the carbon chain of the alkyl group represented by R$^1$ should be no longer than about 30 carbon atoms and more preferably no longer than 20 carbon atoms. Examples of such straight and branched chain alkyl groups which may be represented by R$^1$ include the methyl, ethyl, propyl, isopropyl, butyl, isobutyl, sec-butyl, t-butyl, pentyl, isopentyl, 2-methylbutyl, 1-ethylpropyl, hexyl, isohexyl, heptyl, octyl, isooctyl, nonyl, decyl, 3,7-dimethyloctyl, undecyl, 4,8-dimethylnonyl, dodecyl, tridecyl, isotridecyl, tetradecyl, pentadecyl, 2,6,10-trimethylundecyl, hexadecyl, heptadecyl, octadecyl, nonadecyl, isononadecyl, 2,6,10,14-tetramethylpentadecyl and eicosyl groups. Of these, we particularly prefer the alkyl groups having from 1 to 10 carbon atoms and more preferably the alkyl groups having from 1 to 6 carbon atoms. When $R^1$ represents a substituted alkyl group, the alkyl groups having from 1 to 6 carbon atoms and listed above are preferred, the alkyl groups having from 3 to 5 carbon atoms being particularly preferred.

Where $R^1$ represents a substituted alkyl group, examples of the substituents are given below:

halogen atoms, such as the fluoride, chloride, bromine, and iodine atoms;

hydroxy groups and protected hydroxy groups (for example the aliphatic acyloxy, aromatic acyloxy, α-alkoxyalkoxy, oxygen-containing heterocyclyloxy, trialkylsilyloxy and aralkyloxy groups listed below);

$C_1$–$C_7$ aliphatic acyloxy groups, for example the formyloxy, acetoxy, propionyloxy, butyryloxy, isobutyryloxy and valeryloxy groups;

aromatic acyloxy groups, in which the aryl part is a $C_6$–$C_{10}$ carbocyclic aryl group, for example the benzoyl, 1-naphthoyl and 2-naphthoyl groups, which may be unsubstituted or may have one or more (preferably from 1 to 3) substituents selected from the group consisting of halogen atoms (for example fluorine, chlorine, bromine and iodine atoms), $C_1$–$C_6$ alkyl groups (particularly methyl, ethyl, propyl, isopropyl and butyl groups), and $C_1$–$C_6$ alkoxy groups (particularly methoxy, ethoxy, propoxy, isopropoxy and butoxy groups);

α-alkoxyalkoxy groups, in which each alkoxy part has from 1 to 6 carbon atoms, for example the methoxymethoxy, 1-methoxyethoxy, ethoxymethoxy, 1-ethoxyethoxy and propoxymethoxy groups;

heterocyclyl-oxy groups, in which the heterocyclic ring preferably contains from 3 to 8 ring atoms, of which at least one is an oxygen atom and the remainder may be selected from the group consisting of nitrogen, sulfur and carbon atoms, preferably carbon atoms; these heterocyclic rings are preferably saturated and may be regarded as cyclic ether groups; examples include the tetrahydro-2-furanyloxy and tetrahydro-2-pyranyloxy groups;

trialkylsilyloxy groups, in which the three alkyl groups may be the same or different and each is a $C_1$–$C_6$ alkyl group, for example the trimethylsilyloxy, triethylsilyloxy and t-butyldimethylsilyloxy groups;

aralkyloxy groups, in which the aryl part is a $C_6$–$C_{10}$ carbocyclic aryl group, which is unsubstituted or has from 1 to 3 substituents selected from the substituents defined herein for aryl groups, and the alkyl part is $C_1$–$C_6$ alkyl, preferably $C_1$–$C_3$ alkyl, for example the benzyloxy, p-methoxybenzyloxy or p-bromobenzyloxy groups;

$C_1$–$C_6$ alkoxy groups, which are unsubstituted or have one or more (preferably from 1 to 3, more preferably 1) substituents selected from the group consisting of amino groups, alkylamino groups and dialkylamino groups in which the or each alkyl part is $C_1$–$C_6$ alkyl (for example the methylamino, dimethylamino, ethylamino, diethylamino or propylamino groups); examples of such alkoxy groups include the methoxy, ethoxy, propoxy, isopropoxy and butoxy groups, which may be unsubstituted or may be substituted with the aforementioned amino, alkylamino and dialkylamino groups;

the carboxy group;

alkoxycarbonyl groups, in which the alkoxy part, which may be a straight or branched chain group, has from 1 to 6 carbon atoms, for example the methoxycarbonyl, ethoxycarbonyl, propoxycarbonyl, isopropoxycarbonyl or butoxycarbonyl groups; and carbamoyl, alkylcarbamoyl and dialkylcarbamoyl groups, in which the or each alkyl part has from 1 to 6 carbon atoms, for example the carbamoyl, N-methylcarbamoyl, N,N-dimethylcarbamoyl, N-ethylcarbamoyl, N,N-diethylacarbamoyl or N-propylcarbamoyl groups.

Of these substituents, preferred substituents are the halogen atoms, hydroxy groups, aliphatic acyloxy groups, aromatic acyloxy groups, α-alkoxyalkoxy groups, carboxy groups, heterocyclyl-oxy groups, trialkylsilyloxy groups, aralkyloxy groups and alkoxycarbonyl groups, more preferably the hydroxy, aliphatic acyloxy and benzoyloxy groups. Where the alkyl group represented by $R^1$ is substituted, the maximum number of substituents will, of course, depend upon the size of the alkyl group to be substituted and the steric effects exerted by the substituents; if the alkyl group is small and the substituent bulky, then steric hinderance may limit the number of potential substituents; at the other extreme, if the substituent is small, the number of substituents may ony be limited by the number of available valences of the carbon atoms in the alkyl group for example, where the substituent is a fluorine or chlorine atom, $R^1$ could represent a perfluoroalkyl or perchloroalkyl group. However, in general, from 1 to 3 substituents are preferred, although it should be appreciated that more may be appropriate in specific cases, as is well recognised by those skilled in this art.

Where $R^1$ represents a $C_2$–$C_6$ alkenyl group, this may be a straight or branched chain group and is more preferably a $C_2$–$C_4$ alkenyl group, for example a vinyl, allyl, methallyl or 3-butenyl group.

Where $R^1$ represents an aryl group or a substituted aryl group, the aryl group is preferably a $C_6$–$C_{10}$ carbocyclic aryl group, for example a phenyl, 1-naphthyl or 2-naphthyl group. Where the group is substituted, it may have one or more substituents, which are preferably selected from the group consisting of $C_1$–$C_6$, preferably $C_1$–$C_4$, alkyl groups (for example the methyl, ethyl, propyl, isopropyl or butyl groups), halogen atoms, hydroxy groups, aliphatic acyloxy groups, aromatic acyloxy groups, α-alkoxyalkoxy groups, heterocyclyl-oxy groups, trialkylsilyloxy groups, aralkyloxy groups, alkoxy groups, carboxy groups and alkoxycarbonyl groups. These halogen atoms, aliphatic acyloxy groups, aromatic acyloxy groups, alkoxyalkoxy groups, heterocyclyl-oxy groups, trialkylsilyloxy groups, aralkyloxy groups, alkoxy groups and alkoxycarbonyl groups are the same as the substituents discussed above in relation to alkyl groups and examples of such substituents are given above. In the case of the aryl groups, preferred substituents are hydroxy groups and $C_1$–$C_7$ aliphatic acyloxy groups. The maximum number of substituents may vary depending on steric and other characteristics of the substituent and the aryl group, as is well known in the art. However, from 1 to 3 are preferred, although more may be possible.

Where $R^1$ represents an alkoxycarbonyl group, the alkoxy part preferably has from 1 to 6 carbon atoms, more preferably from 1 to 4 carbon atoms and may be a straight or branched chain group. Examples include the methoxycarbonyl, ethoxycarbonyl, propoxycarbonyl, isopropoxycarbonyl and butoxycarbonyl groups.

In the compounds of formula (I) $R^2$ may represent a hydrogen atom, a $C_1$–$C_6$ alkyl group or a $C_3$ or $C_4$ alkenyl group. Where $R^2$ represents a $C_1$–$C_6$ alkyl group, this may be a straight or branched chain group and examples are the $C_1$–$C_6$ alkyl groups of those exemplified above in relation to $R^1$. Where $R^2$ represents a $C_3$ or $C_4$ alkenyl group, this is preferably an allyl, methallyl or 3-butenyl group.

In the compounds of formula (I), $R^3$ represents a hydrogen atom or a $C_1$–$C_6$ alkyl group. Where $R^3$ represents a $C_1$–$C_6$ alkyl group, this may be a straight or branched chain group and examples are those $C_1$–$C_6$ alkyl groups given above as examples of groups which may be represented by $R^1$.

$R^4$, in the compounds of formula (I), may represent a hydroxy group, a $C_1$–$C_{21}$ aliphatic acyloxy group or an aromatic acyloxy group. Also, for special purposes, the hydroxy group represented by $R^4$ may be protected by formation of, for example, an α-alkoxyalkoxy group, a heterocyclyl-oxy group, a trialkylsilyloxy group or an aralkyloxy group.

Where $R^4$ represents an aliphatic acyloxy group, this has from 1 to 21 carbon atoms and may be a straight or branched chain and saturated or unsaturated group (the term "saturation" here referring to the degree of saturation of carbon-carbon bonds within the aliphatic acyl group), preferably saturated. Preferred examples of such aliphatic acyl groups are the $C_1$–$C_{21}$ alkanoyloxy groups, such as the formyloxy, acetoxy, propionyloxy, butyryloxy, isobutyryloxy, valeryloxy, isovaleryloxy, pivaloyloxy, hexanoyloxy, octanoyloxy, decanoyloxy, lauroyloxy, tridecanoyloxy, myristoyloxy, pentadecanoyloxy, palmitoyloxy, heptadecanoyloxy, stearoyloxy, nonadecanoyloxy, 3,7,11,15-tetramethylhexadecanoyloxy, eicosanoyloxy or heneicosanoyloxy groups. Such groups may be unsubstituted or may have one or more substituents selected from the group consisting of carboxy groups, alkoxycarbonyl groups and aryloxycarbonyl groups, examples of which are given hereinabove.

Where $R^4$ represents an aromatic acyloxy group, this is a group having a carbonyl group attached to a carbon atom of a carbocyclic aryl group, which preferably has from 6 to 10 ring carbon atoms. Examples of such aromatic acyloxy groups include the benzoyloxy, 1-naphthoyloxy and 2-naphthoyloxy groups. These aromatic acyloxy groups may be unsubstituted or may have one or more (preferably from 1 to 3) substituents selected from the group consisting of: $C_1$–$C_6$ alkyl groups, for example the methyl, ethyl, propyl, isopropyl, butyl, isobutyl, sec-butyl, t-butyl, pentyl, isopentyl or hexyl groups; halogen atoms, e.g. as exemplified above as substituents on alkyl groups; hydroxy groups; $C_1$–$C_7$ aliphatic acyloxy groups, e.g. as exemplified above as substituents on alkyl groups; $C_1$–$C_6$ alkoxy groups, e.g. as exemplified above as substituents on alkyl groups; carboxy groups; alkoxycarbonyl groups in which the alkyl part has from 1 to 6 carbon atoms, e.g. as exemplified above as substituents on alkyl groups; and sulfonyloxy groups, particularly alkylsulfonyloxy or arylsulfonyloxy groups, such as the methanesulfonyloxy, ethanesulfonyloxy, propanesulfonyloxy, benzenesulfonyloxy or p-toluenesulfonyloxy groups; of these substituents, the hydroxy, aliphatic acyloxy, carboxy and alkoxycarbonyl groups are preferred.

Where $R^4$ represents a hydroxy group, it will, of course, be appreciated that this group may, if desired, be protected with a conventional protecting group such as those described above with regard to $R^1$, for example, it may be protected if the compound of the invention is subsequently to be used as an intermediate in the synthesis of some other compound; alternatively, it may be protected by a labile protecting group, which can be removed by the patient's metabolism to restore the original hydroxy group; such protecting groups are, of course, well-known in the art and include the acyloxy groups described above. Alternative protecting groups include the α-alkoxyalkoxy, heterocyclyl-oxy, trialkysilyloxy and aralkyloxy groups: these may be as described above for the corresponding groups described as substituents on alkyl groups represented by $R^1$. Other protected hydroxy groups which are possible include heterocyclic acyloxy groups, particularly such groups in which the heterocyclic moiety has one or more, preferably one, hetero-atoms selected from the group consisting of oxygen, sulfur and nitrogen atoms, and has from 4 to 7 ring atoms. Examples of heterocyclic acyloxy groups include the 2-furoyl, 3-thenoyl, 3-pyridinecarbonyl (nicotinoyl) and 4-pyridinecarbonyl groups.

$R^5$ in the compounds of the invention represents a straight or branched chain $C_1$–$C_{12}$ alkyl group, a $C_1$–$C_6$ alkoxy group, a hydroxy group, a $C_1$–$C_7$ aliphatic acyloxy group or an aromatic acyloxy group. Examples of the $C_1$–$C_{12}$ alkyl groups, the alkoxy groups, the aliphatic acyloxy groups and the aromatic acyloxy groups are as given for the corresponding groups represented by $R^1$.

$R^6$ represents a hydrogen atom, a $C_1$–$C_6$ alkyl group or a $C_1$–$C_6$ alkoxy group and examples of such alkyl and alkoxy groups are as given in relation to the corresponding groups represented by $R^1$.

Of the compounds of the invention, we prefer those compounds in which $R^3$ represents a hydrogen atom or a $C_1$–$C_6$ alkyl group, more preferably a $C_1$–$C_6$ alkyl group, and/or $R^5$ represents a $C_1$–$C_6$ alkyl group, and/or $R^6$ represents a hydrogen atom or a $C_1$–$C_6$ alkyl group, more preferably a $C_1$–$C_6$ alkyl group.

In the compounds of the invention, n is 0, 1 or 2, the compounds where n is 1 or 2 being, respectively, cyclic sulfoxides and sulfones. However, we prefer that n should be 0.

In one preferred class of compound of the present invention, $R^1$ represents a hydrogen atom, a $C_1$–$C_{10}$ alkyl group, a $C_1$–$C_{10}$ alkyl group having from 1 to 3 substituents selected from the group consisting of halogen atoms, hydroxy groups, alkoxycarbonyl groups wherein the alkoxy part has from 1 to 6 carbon atoms, $C_1$–$C_7$ aliphatic acyloxy groups, aromatic acyloxy groups, α-alkoxyalkoxy groups wherein both alkoxy parts have from 1 to 6 carbon atoms, heterocyclyl-oxy groups, trialkylsilyloxy groups wherein each alkyl part has from 1 to 6 carbon atoms, aralkyloxy groups wherein the aryl part is $C_6$–$C_{10}$ carbocyclic aryl and the alkyl part is $C_1$–$C_6$ alkyl and carboxy groups, a $C_2$–$C_6$ alkenyl group, a phenyl group or a phenyl group having from 1 to 3 substituents selected from the group consisting of $C_1$–$C_6$ alkyl groups, halogen atoms, hydroxy groups, $C_1$–$C_7$ aliphatic acyloxy groups, aromatic acyloxy groups, α-alkoxyalkoxy groups where each alkoxy part has from 1 to 6 carbon atoms, heterocyclyloxy groups, trialkylsilyloxy groups where each alkyl part has from 1 to 6 carbon atoms and aralkyloxy groups where the aryl part is $C_6$-$C_{10}$ carbocyclic aryl and the alkyl part is $C_1$-$C_6$ alkyl; and $R^2$ represents a hydrogen atom. More preferably, $R^1$ and $R^2$ are as defined above and: $R^3$ represents a hydrogen atom or a $C_1$-$C_6$ alkyl group, more preferably a $C_1$-$C_6$ alkyl group; $R^5$ represents a $C_1$-$C_6$ alkyl group; and $R^6$ represents a hydrogen atom or a $C_1$-$C_6$ alkyl group, more preferably a $C_1$-$C_6$ alkyl group. Still more preferably, $R^1$, $R^2$, $R^3$, $R^5$ and $R^6$ are as defined above and n is 0.

A more preferred class of compounds are those compounds in which: $R^1$ represents a hydrogen atom, a $C_1$-$C_6$ alkyl group, a $C_1$-$C_6$, more preferably $C_3$-$C_5$, alkyl group having from 1 to 3 substituents selected from the group consisting of hydroxy groups, $C_1$-$C_7$ aliphatic acyloxy groups and benzoyloxy groups, a phenyl group, or a phenyl group having from 1 to 3 substituents selected from the group consisting of hydroxy groups and $C_1$-$C_7$ aliphatic acyloxy groups; $R^2$ represents a hydrogen atom; $R^3$ represents a $C_1$-$C_6$ alkyl group; $R^4$ represents a hydroxy group, a $C_1$-$C_7$ aliphatic acyloxy group or a benzoyloxy group; $R^5$ represents a $C_1$-$C_6$ alkyl group; $R^6$ represents a $C_1$-$C_6$ alkyl group; and n is 0.

Where $R^1$ represents a group having a carboxy substituent, the resulting compounds of the invention are capable of forming salts. Such salts may be with metals, ammonia, organic amines or basic amino acids. Examples of suitable metal salts include salts with alkali metals, such as sodium, potassium or lithium, salts with alkaline earth metals, such as calcium or barium, and salts with other pharmaceutically acceptable metals, such as magnesium, aluminum or iron. Examples of organic amines which may form salts include trimethylamine, triethylamine and pyridine, and examples of basic amino acids which may form salts include lysine and arginine.

In the compounds of the invention, where $R^1$ and $R^2$ represent different groups or atoms, the resulting compound can exist in the form of optical isomers; the present invention envisages both the individual isolated isomers and mixtures (e.g. racemates) thereof. Where the compound is prepared (as is common) in the form of a mixture of isomers, these may, if desired, be separated by resolution means so well known as to require no elucidation here. Alternatively, the mixture may be used as such.

Of the compounds of the invention, examples are given in the following list:
1. 5-Acetoxy-2,4,6,7-tetramethyl-1,3-benzoxathiole
2. 2-Ethyl-4,6,7-trimethyl-5-propionyloxy-1,3-benzoxathiole
3. 5-Butyryloxy-4,6,7-trimethyl-2-propyl-1,3-benzoxathiole
4. 5-Isobutyryloxy-2-isopropyl-4,6,7-trimethyl-1,3- benzoxathiole
5. 2-Butyl-4,6,7-trimethyl-5-valeryloxy-1,3-benzoxathiole
6. 5-Heptanoyloxy-2-hexyl-4,6,7-trimethyl-1,3-benzoxathiole
7. 2-Heptyl-4,6,7-trimethyl-5-octanoyloxy-1,3-benzoxathiole
8. 5-Arachidyloxy-4,6,7-trimethyl-2-nonadecyl-1,3-benzoxathiole
9. 4,6,7-Trimethyl-5-(3,7,11,15-tetramethylhexadecanoyloxy)-2-(2,6,10,14-tetramethylpentadecyl)-1,3-benzoxathiole
10. Methyl 3-[5-(3-methoxycarbonylpropionyloxy)-4,6,7-trimethyl-1,3-benzoxathiole-2-yl]propionate.
11. Ethyl 3-[5-(3-ethoxycarbonylpropionyloxy)-4,6,7-trimethyl-1,3-benzoxathiole-2-yl]propionate
12. Butyl 3-[5-(3-butoxycarbonylpropionyloxy)-4,6,7-trimethyl-1,3-benzoxathiole-2-yl]propionate
13. 5-Benzoyloxy-4,6,7-trimethyl-2-phenyl-1,3-benzoxathiole
14. 5-(o-Acetoxybenzoyloxy)-2-(o-acetoxyphenyl)-4,6,7-trimethyl-1,3-benzoxathiole
15. Methyl 4-[5-(p-methoxycarbonylbenzoyloxy)-4,6,7-trimethyl-1,3-benzoxathiole-2-yl]benzoate
16. 5-(p-Chlorobenzoyloxy)-2-(p-chlorophenyl)-4,6,7-trimethyl-1,3-benzoxathiole
17. 5-Acetoxy-6,7-dimethoxy-2,4-dimethyl-1,3-benzoxathiole
18. 5,6-Diacetoxy-2,4,7-trimethyl-1,3-benzoxathiole
19. 5-Hydroxy-2,4,6,7-tetramethyl-1,3-benzoxathiole
20. 2-Ethyl-5-hydroxy-4,6,7-trimethyl-1,3-benzoxathiole
21. 5-Hydroxy-4,6,7-trimethyl-2-propyl-1,3-benzoxathiole
22. 5-Hydroxy-2-isopropyl-4,6,7-trimethyl-1,3-benzoxathiole
23. 2-Butyl-5-hydroxy-4,6,7-trimethyl-1,3-benzoxathiole
24. 2-Hexyl-5-hydroxy-4,6,7-trimethyl-1,3-benzoxathiole
25. 2-Heptyl-5-hydroxy-4,6,7-trimethyl-1,3-benzoxathiole
26. 5-Hydroxy-4,6,7-trimethyl-2-nonadecyl-1,3-benzoxathiole
27. 5-Hydroxy-4,6,7-trimethyl-2-(2,6,10,14-tetramethylpentadecyl)-1,3-benzoxathiole
28. 3-(5-Hydroxy-4,6,7-trimethyl-1,3-benzoxathiole-2-yl)propionic acid
29. 5-Hydroxy-4,6,7-trimethyl-2-phenyl-1,3-benzoxathiole
30. 5-(o-Hydroxybenzoyloxy)-2-(o-hydroxyphenyl)-4,6,7-trimethyl-1,3-benzoxathiole
31. 5-Hydroxy-2-(o-hydroxyphenyl)-4,6,7-trimethyl-1,3-benzoxathiole
32. 4-(5-Hydroxy-4,6,7-trimethyl-1,3-benzoxathiole-2-yl)benzoic acid
33. 5-t-Butyldimethylsilyloxy-4,6,7-trimethyl-2-phenyl-1,3-benzoxathiole
34. 5-t-Butyldimethylsilyloxy-2,4,6,7-tetramethyl-2-phenyl-1,3-benzoxathiole
35. 2-Butyl-5-t-butyldimethysilyloxy-4,6,7-trimethyl-2-phenyl-1,3-benzoxathiole
36. 2-Allyl-5-t-butyldimethylsilyloxy-4,6,7-trimethyl-2-phenyl-1,3-benzoxathiole
37. 5-Hydroxy-2,4,6,7-tetramethyl-2-phenyl-1,3-benzoxathiole
38. 2-Butyl-5-hydroxy-4,6,7-trimethyl-2-phenyl-1,3-benzoxathiole
39. 2-Allyl-5-hydroxy-4,6,7-trimethyl-2-phenyl-1,3-benzoxathiole
40. 5-Hydroxy-2,2,4,6,7-pentamethyl-1,3-benzoxathiole
41. 5-(1-Ethoxyethoxy)-4,6,7-trimethyl-1,3-benzoxathiole
42. 5-Hydroxy-4,6,7-trimethyl-1,3-benzoxathiole
43. 5-Benzoyloxy-2,4,6,7-tetramethyl-1,3-benzoxathiole
44. 5-p-Methoxycarbonylbenzoyloxy-2,4,6,7-tetramethyl-1,3-benzoxathiole
45. 5-o-Acetoxybenzoyloxy-2,4,6,7-tetramethyl-1,3-benzoxathiole
46. 5-(3-Methoxycarbonylpropionyloxy)-2,4,6,7-tetramethyl-1,3-benzoxathiole 47. Methyl 3-(5-hydroxy-4,6,7-trimethyl-1,3-benzoxathiole-2-yl)propionate
48. 3-(5-Hydroxy-4,6,7-trimethyl-1,3-benzoxathiole-2-yl)propionamide
49. 3-(5-Hydroxy-4,6,7-trimethyl-1,3-benzoxathiole-2-yl)propanol
50. 5-Acetoxy-2-(3-acetoxypropyl)-4,6,7-trimethyl-1,3-benzoxathiole
51. 5-Benzoyloxy-2-(3-benzoyloxypropyl)-4,6,7-trimethyl-1,3-benzoxathiole
52. 5-Hydroxy-2-(3-iodopropyl)-4,6,7-trimethyl-1,3-benzoxathiole
53. 5-Formyloxy-2-(3-iodopropyl)-4,6,7-trimethyl-1,3-benzoxathiole
54. 2-(3-Bromopropyl)-5-hydroxy-4,6,7-trimethyl-1,3-benzoxathiole
55. 2-(3-Bromopropyl)-5-formyloxy-4,6,7-trimethyl-1,3-benzoxathiole
56. 2-(3-Chloropropyl)-5-hydroxy-4,6,7-trimethyl-1,3-benzoxathiole
57. 2-(3-Chloropropyl)-4,6,7-trimethyl-5-(p-tosyloxy)-1,3-benzoxathiole
58. 5-t-Butyldimethylsilyloxy-2-(3-chloropropyl)-4,6,7-trimethyl-1,3-benzoxathiole
59. 5-t-Butyldimethylsilyloxy-2-(3-iodopropyl)-4,6,7-trimethyl-1,3-benzoxathiole
60. 5-(5-t-Butyldimethylsilyloxy-4,6,7-trimethyl-1,3-benzoxathiole-2-yl)-2,2-dimethylpentanoic acid
61. 5-(5-Hydroxy-4,6,7-trimethyl-1,3-benzoxathiole-2-yl)-2,2-dimethylpentanoic acid
62. 5-(5-Hydroxy-4,6,7-trimethyl-1,3-benzoxathiole-2-yl)-2,2-dimethylpentanol
63. 5-Hydroxy-2-(3-methoxymethoxypropyl)-4,6,7-trimethyl-1,3-benzoxathiole
64. 5-Acetoxy-2-(3-methoxymethoxypropyl)-4,6,7-trimethyl-1,3-benzoxathiole
65. 3-(5-Methoxymethoxy-4,6,7-trimethyl-1,3-benzoxathiole-2-yl)propanol
66. 2-(3-Iodopropyl)-5-methoxymethoxy-4,6,7-trimethyl-1,3-benzoxathiole
67. 2-(3-Bromopropyl)-5-methoxymethyl-4,6,7-trimethyl-1,3-benzoxathiole
68. 2-[3-(2-Dimethylaminoethoxy)propyl]-5-methoxymethoxy-4,6,7-trimethyl-1,3-benzoxathiole
69. 2-Allyl-5-methoxymethoxy-4,6,7-trimethyl-1,3-benzoxathiole
70. 2-[3-(2-Dimethylaminoethoxy)propyl]-5-hydroxy-4,6,7-trimethyl-1,3-benzoxathiole
71. 2-Allyl-5-hydroxy-4,6,7-trimethyl-1,3-benzoxathiole
72. 5-t-Butyldimethylsilyloxy-4,6,7-trimethyl-1,3-benzoxathiole
73. 5-t-Butyldimethylsilyloxy-4,6,7-trimethyl-1,3-benzoxthiole-3-oxide
74. 5-Acetoxy-4,6,7-trimethyl-2-propyl-1,3-benzoxathiole
75. 5-Benzoyloxy-4,6,7-trimethyl-2-propyl-1,3-benzoxathiole
76. 6-t-Butyl-5-hydroxy-2-propyl-1,3-benzoxathiole
77. 5-Acetoxy-6-t-butyl-2-propyl-1,3-benzoxathiole
78. 6-t-Butyl-5-butyryloxy-2-propyl-1,3-benzoxathiole
79. 5-Benzoyloxy-6-t-butyl-2-propyl-1,3-benzoxathiole
80. 6-t-Butyl-5-hydroxy-2-methyl-1,3-benzoxathiole
81. 5-Acetoxy-6-t-butoxy-2-methyl-1,3-benzoxathiole
82. 6-t-Butyl-5-butyryloxy-2-methyl-1,3-benzoxathiole
83. 6-t-Butyl-5-hydroxy-1,3-benzoxathiole
84. 6-t-Butyl-2-hexyl-5-hydroxy-1,3-benzoxathiole
85. 6-t-Butyl-5-hydroxy-2-phenyl-1,3-benzoxathiole
86. 3-(6-t-butyl-5-hydroxy-1,3-benzoxathiole-2-yl)propanol
87. 5-Acetoxy-2-(3-acetoxypropyl)-6-t-butyl-1,3-benzoxathiole
88. 5-Benzoyloxy-2-(3-benzoyloxypropyl)-6-t-butyl-1,3-benzoxathiole Of the compounds of the invention, preferred compounds are those listed above and numbered as 1, 19, 20, 21, 22, 23, 24, 28, 29, 31, 42, 43, 47, 49, 71, 74, 75, 76, 77, 80, 81, 82 and 86, more preferred compounds are those numbered as 19, 21, 42 and 49, and the most preferred compounds are those numbered as 21 and 49.

Of the compounds listed above, all, save only Nos. 40, 41, 42, 72, 73 and 83, can exist in the form of optical isomers, as a result of asymmetry at the 2-position.

A preferred method of preparing the compounds of the invention comprises reacting a dithio or trithio compound of formula (II):

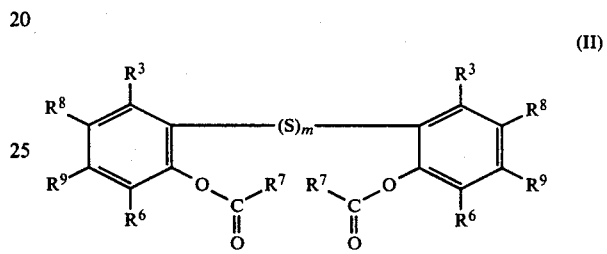

(in which: $R^3$ and $R^6$ are as defined above; $R^7$ represents a hydrogen atom, an alkyl group, an alkyl group having at least one substituent selected from the group consisting of protected hydroxy groups, alkoxycarbonyl groups where the alkoxy part has from 1 to 6 carbon atoms and $C_1$–$C_6$ alkoxy groups, a $C_2$–$C_6$ alkenyl group, an aryl group, an aryl group having at least one of the substituents heretofor described for aryl groups in which any hydroxy group is protected, or an alkoxycarbonyl group in which the alkoxy part has from 1 to 6 carbon atoms; $R^8$ represents a protected hydroxy group; and $R^9$ represents any one of the groups represented by $R^5$, but in which any hydroxy group is protected; and m is 2 or 3) with a reducing agent, preferably in an inert solvent, to give a compound of formula (III):

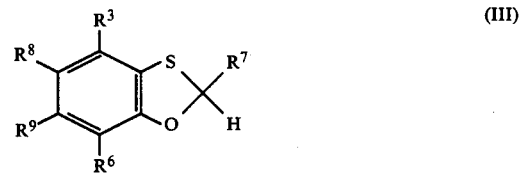

(in which $R^3$, $R^6$, $R^7$, $R^8$ and $R^9$ are as defined above); and, if necessary, in any order removing protecting groups and oxidizing the sulfur atom to give a compound of formula (Ia):

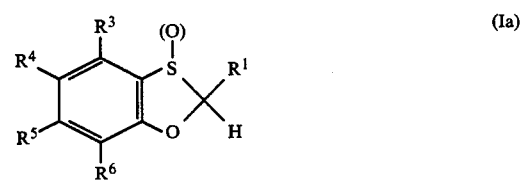

(in which $R^1$, $R^3$, $R^4$, $R^5$, $R^6$ and n are as defined above).

This method is described in more detail along with the preparation of its starting material and several alternative methods in the following Methods.

Method A

Compounds of formula (I) in which $R^2$ represents, as is preferred, a hydrogen atom, that is to say compounds of formula (Ia), may be prepared as illustrated by the following reaction scheme:

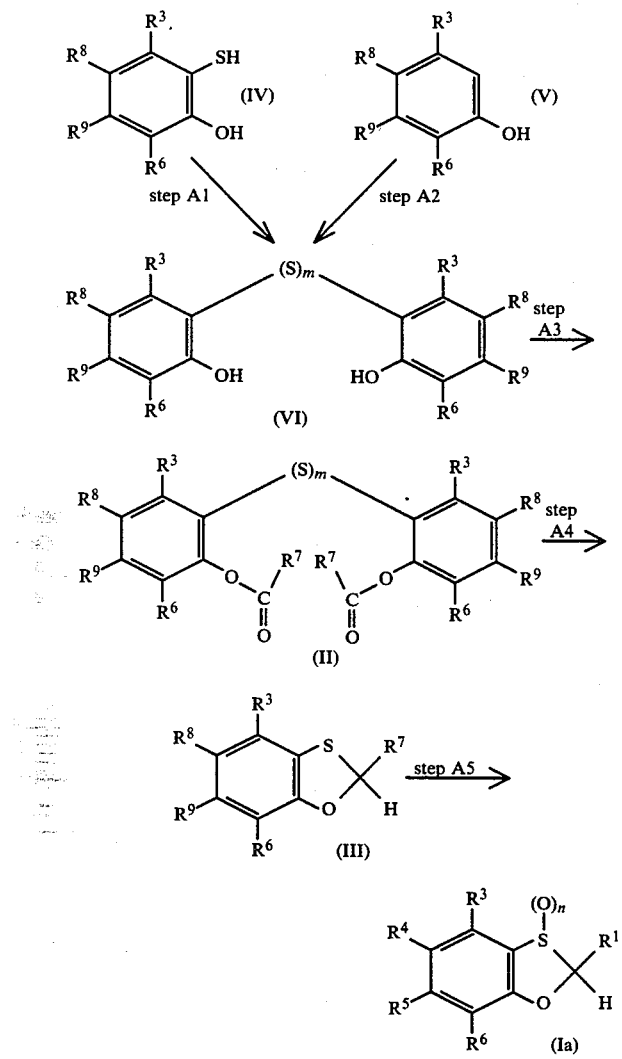

In the above formulae, $R^1$, $R^3$, $R^4$, $R^5$, $R^6$, $R^7$, $R^8$, $R^9$, m and n are as defined above.

In step A1 of this method, a dithio or trithio compound of formula (VI) is prepared by reacting a thiol of general formula (IV) with oxygen in the presence of an inert solvent. The compound of formula (IV) used as starting material in this step can be prepared by hydrolysis of the known compound, 2-oxo-1,3-benzoxathiole [see, for example, J. Org. Chem., 33,4426 (1968)] with an alkali.

There is no particular limitation on the nature of the solvent employed in this step, provided that it does not interfere with the reaction. Examples of suitable solvents include: aliphatic hydrocarbons, such as hexane, heptane or octane; aromatic hydrocarbons, such as benzene, toluene or xylene; halogenated hydrocarbons, such as methylene chloride, chloroform or carbon tetrachloride; ethers, such as diethyl ether, tetrahydrofuran or dioxane; and amides, such as dimethylformamide or dimethylacetamide. The ethers or halogenated hydrocarbons are preferred.

The reaction can take place over a wide temperature range, e.g. from 0° to 100° C., a temperature within the range from 10° to 40° C. generally being most convenient. The time required for the reaction will depend upon various factors, including the nature of the starting material and the reaction temperature, but a period of from 1 to 50 hours will usually suffice.

Oxygen may be introduced into the reaction mixture in various ways, for example by passing oxygen or air through the reaction solution or simply by stirring the reaction solution in an atmosphere of oxygen or air; the reaction generally proceeds more efficiently if air is passed through the reaction solution.

After completion of the reaction, the desired product of formula (VI) may be recovered from the reaction mixture by conventional means. For example, the organic solvent may be distilled from the reaction mixture and then the residue purified by conventional techniques, such as recrystallization or the various chromatography techniques, e.g. column chromatography.

Step A2 is an alternative to step A1 for preparing the dithio or trithio compound of formula (VI) and is achieved by reacting a hydroxy compound of formula (V) with a halogenated sulfur compound in the presence or absence of a catalyst and in an inert solvent. Suitable halogenated sulfur compounds include sulfur monochloride, sulfur monobromide and sulfur dichloride, of which sulfur monochloride is preferred. Where a catalyst is employed, this is preferably a metal powder, for example a powder of iron, nickel or cobalt, preferably iron powder. However, the reaction takes place even in the absence of a catalyst to give the desired product.

The nature of the solvent employed for this reaction is not critical, provided that it does not interfere with the reaction; suitable solvents include: nitriles, such as acetonitrile; ethers, such as diethyl ether, tetrahydrofuran or dioxane; and amides, such as dimethylformamide or dimethylacetamide. Of these, acetonitrile is preferred.

The reaction will take place over a wide range of temperatures, although relatively low temperatures are generally preferred, in order to reduce or control side reactions. A suitable temperature range is from $-70°$ C. to $+30°$ C., more preferably from $-30°$ C. to $+10°$ C. The time required for the reaction will vary depending upon many factors, including the nature of the reagents and the reaction temperature, but a period of from 1 to 20 hours, more commonly from 2 to 10 hours, will normally suffice.

Further control of side reactions may be achieved by carrying out the reaction in an atmosphere of an inert gas, for example nitrogen or argon.

The product of this reaction will normally be a mixture of dithio and trithio compounds.

After completion of the reaction, the desired product of formula (VI) may be recovered from the reaction mixture by conventional means. For example, one suitable recovery procedure comprises filtering off insolubles, distilling the organic solvent from the filtrate and then purifying the residue by conventional means, such as recrystallization or the various chromatography techniques, particularly column chromatography. If desired, the dithio and trithio compounds may be separated from each other, but we generally prefer that the mixture of dithio and trithio compounds should be used in the next step without prior isolation.

In step A3, an acyloxy compound of formula (II) is prepared by reacting the dithio or trithio compound of formula (VI) with a carboxylic acid of formula (VII):

$$R^{10}COOH \qquad (VII)$$

(in which $R^{10}$ represents any of the groups represented by $R^7$, but not a hydrogen atom) or with a reactive derivative of this carboxylic acid (VII). Examples of reactive derivatives include the carboxylic acid halides of formula $R^{10}COX$ (in which $R^{10}$ is as defined above and X represents a halogen atom, preferably a chlorine, bromine or iodine atom) or an acid anhydride of formula $R^{11}$-C(:O)-O-C(:O)-$R^{11}$ (in which $R^{11}$ represents any one of the groups represented by $R^{10}$ except the alkoxycarbonyl group). Of these, the carboxylic acid chlorides are preferred.

It is also possible to employ a cyclic acid anhydride of a dicarboxylic acid, for example succinic anhydride or glutaric anhydride; in this case, the product will be a compound of formula (II) in which $R^7$ represents an alkyl or aryl group having a carboxy substituent.

The reaction is preferably carried out in the presence of an inert solvent, the nature of which is not critical, provided that it does not interfere with the reaction. Suitable solvents include, for example: aliphatic hydrocarbons, such as hexane, heptane or octane; aromatic hydrocarbons, such as benzene, toluene or xylene; halogenated hydrocarbons, such as methylene chloride or chloroform; and ethers, such as diethyl ether, tetrahydrofuran or dioxane; of these, the aromatic hydrocarbons or ethers are preferred.

Particularly where a carboxylic acid halide or anhydride is employed, the reaction is preferably effected in the presence of an acid-binding agent, which removes from the reaction medium the hydrogen halide or other acid produced by the reaction and thus accelerates the reaction. Suitable acid-binding agents include: organic bases, such as triethylamine, N,N-dimethylaniline, N-methylmorpholine, pyridine, 4-(N,N-dimethylamino)-pyridine, 1,5-diazabicyclo[4.3.0]non-5-ene or 1,8-diazabicyclo[5.4.0]undec-7-ene; or an inorganic base, such as sodium hydroxide, potassium hydroxide, sodium carbonate, potassium carbonate or sodium bicarbonate. Of these, the organic bases, particularly triethylamine or pyridine are preferred and, if an excess of such a base is used, then an additional solvent may be unnecessary.

The reaction temperature may vary over a wide range, for example from $-10°$ C. to $+60°$ C., but we generally find it convenient to carry out the reaction at about room temperature. The time required for the reaction will vary depending upon many factors, but particularly upon the nature of the reagents and the reaction temperature; however, a period of from 30 minutes to 48 hours, more commonly from 10 to 30 hours, will usually suffice.

Compounds of formula (II) in which $R^7$ represents a hydrogen atom can easily be prepared by carrying out a standard Vilsmeier reaction on the compound of formula (VI).

After completion of the reaction, the desired compound of formula (II) may be recovered from the reaction mixture by conventional means. For example, one suitable recovery procedure comprises: pouring the reaction mixture into ice-water, extracting the mixture with an organic solvent; and then distilling the solvent from the extract, to leave the desired product. This may, if necessary, be further purified by various conventional techniques, such as recrystallization or the various chromatography techniques, particularly column chromatography.

In step A4, a compound of formula (III) is prepared by reacting the compound of formula (II) with a reducing agent in an inert solvent.

A wide variety of reducing agents may be employed for this reaction and the nature of the reducing agent is not critical, provided that it does not damage other parts of the molecule. Suitable reducing agents include: lower oxidation state halides of metals which can exist in two or more oxidation states, for example stannous chloride; and metal powders in association with an acid, for example powders of iron, zinc or tin, preferably zinc or iron. The acids employed are preferably those defined below for use as solvents.

The reaction will normally be carried out in the presence of a solvent, the nature of which is not critical, provided that it does not adversely affect (although it may participate in) the reaction. Suitable solvents include: water; alcohols, such as methanol, ethanol, propanol, butanol or isobutanol; and aliphatic acids, such as acetic acid, propionic acid, butyric acid, valeric acid or isovaleric acid. Of these, we prefer the aliphatic acids, such as acetic acid or propionic acid, and these, as mentioned above, may participate in the reaction where the reducing agent is a metal powder.

For carrying out this reaction, we prefer that the starting material of formula (II) should be a compound in which $R^7$ represents an optionally substituted alkyl group or an optionally substituted aryl group.

The reaction will take place over a very wide range of temperatures, the precise temperature chosen being not particularly critical. A suitable temperature would be within the range from $0°$ C. to $200°$ C., more preferably from $50°$ C. to $100°$ C. The time required for the reaction will vary depending upon many factors, including the nature of the starting material, the nature of the reducing agent and the reaction temperature, but a period of from 1 to 30 hours, more commonly from 3 to 20 hours, will usually suffice.

After completion of the reaction, the desired product of formula (III) may be recovered from the reaction mixture by conventional means. For example, one suitable recovery procedure comprises: filtering off any insolubles produced; and distilling off the organic solvent to give the desired product as a residue; if necessary, an organic solvent may be added to this residue to extract the desired compound, the extract may be washed with water and then the solvent distilled off to leave a purified form of the desired compound. If necessary, the product may be further purified by conventional means, for example recrystallization or the various chromatography techniques, particularly column chromatography.

The resulting compound of formula (III) may, depending upon the values of $R^7$, $R^8$ and $R^9$, be the desired final product of the reaction sequence, in which case step A5 need not be carried out.

The step A5 embraces the following reactions, all of which are optional, and any one or more of which may be carried out, as necessary to achieve the desired final product: elimination of hydroxy-protecting groups from $R^7$ and/or $R^8$ and/or $R^9$ in the compound of formula (III); oxidation of a resulting hydroxymethyl group to a carboxy group; esterification of the carboxy group; conversion of an alkoxycarbonyl group included in the group represented by $R^7$ to a carboxy group, to an optionally substituted carbamoyl group or to a hydroxymethyl group; conversion of a resulting hydroxymethyl group to a halomethyl group; reaction of the resulting halide with an anion (for example a carbanion or oxyanion); conversion of a haloalkyl group to an alkenyl group by elimination of a hydrogen halide; oxidation of the compound to convert the ring sulfur atom to a sulfoxide or sulfone group; and protection of any hydroxy group. Except where clearly noted above, the precise sequence of these reactions is unimportant and the reactions may be carried out in any order. The reactions are described in more detail below.

Elimination of the hydroxy-protecting group or groups is, of course, a very well-known reaction and may be carried out by conventional means, the precise reactions chosen depending upon the precise nature of the hydroxy-protecting group. Where the compound contains two or more hydroxy-protecting groups, these may be chosen so that all or some of them are removed together by a single reaction or they may be chosen so that they are not all removable by a single reaction, so as to leave one or more of the hydroxy groups protected in the final product.

If the hydroxy-protecting group is an aliphatic acyl or aromatic acyl group, it may be eliminated by a conventional hydrolysis reaction. Such a reaction is normally carried out by treating the compound with an acid or a base, the nature of the acid or base being not critical and any such acid or base commonly used for hydrolysis reactions may be employed in the present invention. Most commonly and also preferably in the present case, such reactions are carried out under basic conditions, using as the base: ammonia or an organic amine; an alkali metal hydroxide, such as lithium hydroxide, sodium hydroxide or potassium hydroxide; or an alkaline earth metal hydroxide, such as calcium hydroxide or barium hydroxide. There is likewise no particular limitation on the nature of the solvent to be employed in this reaction and any solvent commonly used for hydrolysis may equally be used in the present invention. Examples of such solvents include: alcohols, such as methanol, ethanol, propanol or isopropanol; ethers, such as diethyl ether, tetrahydrofuran, dioxane or ethylene glycol dimethyl ether; dialkyl sulfoxides, such as dimethyl sulfoxide; or a mixture of any one or more of these organic solvents with water. The reaction temperature is not particularly critical and the reaction will take place over a wide temperature range, but we normally prefer to employ a temperature within the range from room temperature to the boiling point of the solvent employed. The time required for the reaction will vary depending upon many factors, primarily upon the reaction temperature, but a period of from 1 to 24 hours will normally suffice. It should be noted that, if the compound contains an alkoxycarbonyl group or an aryloxycarbonyl group, then this hydrolysis reaction will generally convert the group to a free carboxy group. These protecting groups may also be removed by treating the compound with a reducing agent, such as lithium aluminum hydride, in a suitable solvent, such as tetrahydrofuran.

If the hydroxy-protecting group is an α-alkoxyalkyl group or a heterocyclic (cyclic ether) group, this may easily be removed by contacting the compound with an acid. The nature of the acid employed is not critical and a very wide range of acids may be used. Examples of such acids include: organic carboxylic acids, such as formic acid, acetic acid, trifluoroacetic acid, propionic acid, butyric acid, oxalic acid or malonic acid; an organic sulfonic acid, such as methanesulfonic acid, benzenesulfonic acid, p-toluenesulfonic acid or camphorsulfonic acid; a mineral acid, such as hydrochloric acid, hydrobromic acid or sulfuric acid; or a solid Lewis acid, such as silica gel or alumina. The reaction may be carried out in the presence or absence of a solvent, but we normally prefer to employ a solvent, as this enables the reaction to proceed more smoothly. Where a solvent is employed, its nature is not critical, provided that it does not adversely affect the reaction. Examples of suitable solvents include: water; alcohols, such as methanol or ethanol; ethers, such as tetrahydrofuran or dioxane; ketones, such as acetone or methyl ethyl ketone; halogenated hydrocarbons, such as chloroform, methylene chloride, 1,2-dichloroethane or methylene dibromide; or a mixture of one or more of these organic solvents with water. The reaction will take place over a wide range of temperatures and the reaction temperature is not particularly critical; however, we generally prefer to carry out the reaction at a temperature within the range from room temperature to the boiling point of the solvent (if any) or reaction medium. The time required for the reaction will vary, depending upon many factors, including the reaction temperature and the nature of the reagents, but a period of from 30 minutes to 10 hours will normally suffice.

Where the hydroxy-protecting group is a trialkylsilyl group, this may easily be removed by contacting the compound with an aqueous acid or base. A wide variety of acids and bases may be used, if desired, and the precise nature of that compound is not critical to the present invention. Examples of suitable acids and bases include: organic acids, particularly organic carboxylic acids, such as formic acid, acetic acid, propionic acid, butyric acid, oxalic acid or malonic acid; mineral acids, such as hydrochloric acid, hydrobromic acid or sulfuric acid; alkali metal hydroxides, such as sodium hydroxide or potassium hydroxide; alkaline earth metal hydroxides, such as calcium hydroxide; alkali metal carbonates, such as sodium carbonate or potassium carbonate; and alkaline earth metal carbonates, such as calcium carbonate. When water is employed as the reaction solvent, other solvents are not necessary. However, if desired, the reaction solvent may comprise a mixture of water with an organic solvent, for example: an ether, such as tetrahydrofuran or dioxane; or an alcohol, such as methanol or ethanol. The reaction temperature is not particularly critical as the reaction will take place over a wide temperature range, but, for convenience, the reaction is most commonly carried out at about room temperature. The time required for the reaction will vary, depending upon many factors, including the reaction temperature and the nature of the reagents; however, a period of from 30 minutes to 5 hours will normally suffice. The same protecting groups may also be removed by treating the compound with tetrabutylammonium fluoride in a suitable solvent, for example: an ether, such as tetrahydrofuran or dioxane; or an aliphatic acid, such as acetic acid.

If the hydroxy-protecting group is an aralkyl or benzhydryl group, it may be removed by treating the compound with a suitable reducing agent, for example:

hydrogen in the presence of a catalyst, such as platinum- or palladium-on-charcoal; or an alkali metal sulfide, such as sodium sulfide or potassium sulfide. The reaction is usually carried out in the presence of a solvent, the nature of which is not critical, provided that it does not interface with the reaction. Examples of suitable solvents include: alcohols, such as methanol or ethanol; ethers, such as tetrahydrofuran or dioxane; aliphatic acids, such as acetic acid; or a mixture of any one or more of these organic solvents with water. The reaction temperature may vary over a wide range, although a relatively low temperature is normally preferred in order to control the reduction, for example a temperature from 0° C. to about room temperature. The time required for the reaction will vary, depending upon the nature of the starting material and the nature of the reducing agent, as well as the reaction temperature, but a period of from 5 minutes to 12 hours will normally suffice. When the hydroxy-protecting group in the group represented by $R^7$ is the same as that in the group represented by $R^8$ or is of the same class of protecting groups as that in the group represented by $R^8$, the protecting groups may be removed simultaneously; however, they can also be removed selectively by appropriate choice of protecting group and removal reaction.

Conversion of a hydroxymethyl group in the compound to a carboxy group may be carried out by conventional means employing an oxidizing agent. Suitable oxidizing agents include: chromic anhydride/concentrated sulfuric acid/water (Jones' reagent); potassium permanganate/sodium hydroxide; potassium permanganate/sodium carbonate; silver oxide; or potassium bichromate/sulfuric acid. The reaction is preferably effected in the presence of a solvent, the nature of which is not critical, provided that it does not adversely affect the reaction. Suitable solvents include: ketones, such as acetone; water; or a mixture of water with an alcohol, such as methanol or ethanol. The reaction will take place over a wide temperature range and the precise reaction temperature is not particularly critical; a suitable temperature may be within the range from $-30°$ C. to $+100°$ C. The time required for the reaction will vary depending upon many factors including the nature of the reagents and the reaction temperature, but a period of from 30 minutes to 5 hours will normally suffice.

The oxidization reaction may oxidize the ring sulfur atom to a sulfoxide or sulfone group; if it does, these may be converted back to an unoxidized sulfur atom by treatment with a reducing agent, such as thiophenol, sodium sulfite or lithium aluminum hydride, by conventional means.

Esterification of a carboxy group in the compound may be carried out in the presence or absence of a solvent by contacting the compound with an esterifying agent. Any esterifying agent capable of forming an ester with a carboxy compound may be used and the nature of such an agent will depend upon the intended final product. Suitable esterifying agents include: diazoalkanes, such as diazomethane, diazoethane, diazopropane, diazoisopropane or diazobutane; alcohols capable of forming esters, such as methanol, ethanol, propanol, isopropanol or butanol, in the presence of a mineral acid (such as hydrochloric acid, hydrobromic acid or sulfuric acid) or of an organic acid (such as methanesulfonic acid, benzenesulfonic acid or p-toluenesulfonic acid); or a $C_1$-$C_6$ alkyl halide, particularly an alkyl bromide, such as methyl bromide or ethyl bromide, in the presence of a base (for example sodium hydroxide, potassium hydroxide or sodium carbonate). When a diazoalkane is used as the esterifying agent, the reaction is preferably carried out in the presence of a solvent, the nature of which is not critical, provided that it does not interfere with the reaction. Suitable solvents include the ethers, such as diethyl ether or dioxane. The reaction temperature is likewise not critical, but a relatively low temperature is desirable, in order to reduce or control side reactions and to inhibit decomposition of the diazoalkane; accordingly, the reaction is normally carried out under ice-cooling. If the esterifying agent is an alcohol in the presence of an acid, we prefer that the solvent should be provided by an excess of the alcohol. In this case, the reaction temperature is not critical, but we prefer a temperature within the range from room temperature to the boiling point of the alcohol employed. The time required for these reactions will vary depending upon many factors, including the reaction temperature and the nature of the reagents, but a period of from 1 hour to 2 days will normally suffice.

When an alkyl halide is employed as the esterifying agent, the reaction is preferably effected in the presence of a solvent, the nature of which is not critical, provided that it has no adverse effect on the reaction. Suitable solvents include: ethers, such as tetrahydrofuran, dioxane or diethyl ether; aliphatic and aromatic hydrocarbons, such as hexane, heptane, benzene, toluene or xylene; halogenated hydrocarbons, such as methylene chloride, 1,2-dichloroethane or carbon tetrachloride; amides, such as dimethylformamide or dimethylacetamide; or sulfoxides, such as dimethyl sulfoxide. The reaction will take place over a wide range of temperatures, conveniently from 0° to 100° C. The time required for the reaction will vary depending on many factors, particularly the nature of the reagents and the reaction temperature, but a period of from several minutes to several hours will normally suffice.

Conversion of an alkoxycarbonyl group to a free carboxy group may be carried out employing the same reactions as are used to remove hydroxy-protecting groups, when these protecting groups are aliphatic acyl or aromatic acyl groups.

Conversion of an alkoxycarbonyl group to an optionally substituted carbamoyl group may be effected by contacting a compound containing an alkoxycarbonyl group with an amine in the presence of a solvent. The nature of the amine is not critical, provided that it is capable of forming an amide by reaction with an ester group, and the precise choice of amine will be dictated primarily by the nature of the optionally substituted carbamoyl group which it is desired to prepare. Examples of suitable amines include ammonia and such primary and secondary amines as: methylamine; ethylamine; propylamine; isopropylamine; butylamine; aniline; p-methylaniline; dimethylamine; methylethylamine; diethylamine; N-methylaniline; N-ethylaniline; and N,m-dimethylaniline. The reaction is preferably carried out in the presence of a solvent, the nature of which is not critical, provided that it does not adversely affect the reaction. Suitable solvents include: water; ethers, such as diethyl ether, tetrahydrofuran or dioxane; and alcohols, such as methanol or ethanol. The reaction may be carried out over a wide range of temperatures, as the precise reaction temperature is not particularly critical; however, a temperature within the range from 0° C. to 100° C. is normally convenient and preferred. The time required for the reaction will vary depending upon many factors, including the nature of the reagents and the reaction temperature, but a period of from 1 hour to 7 days will normally suffice.

Conversion of an alkoxycarbonyl or carboxy group to a hydroxymethyl group may be achieved be treating a compound containing the aforesaid alkoxycarbonyl or carboxy group with a reducing agent in an inert solvent. The nature of the reducing agent is not critical, but it should be capable of converting the alkoxycarbonyl or carboxy group to a hydroxymethyl group without damaging or damaging to any significant extent the remainder of the molecule; such reducing agents are well-known in the art. Examples include such aluminum compounds as lithium aluminum hydride and sodium bis(2-methoxyethoxy)aluminum hydride. The nature of the solvent employed is not critical, provided that it does not adversely affect the reaction. Suitable solvents include: ethers, such as diethyl ether, tetrahydrofuran or dioxane; and hydrocarbons, which may be aliphatic, cycloaliphatic or aromatic, such as hexane, cyclohexane, benzene, toluene or xylene; of these, the ethers are preferred. The reaction will take place over a wide temperature range and the precise reaction temperature is not particularly critical; a temperature within the range from 10° to 100° C. is normally preferred. The time required for the reaction will vary depending upon many factors, including the reaction temperature and the nature of the reagents, but a period of from 30 minutes to 10 hours will normally suffice.

Conversion of the hydroxymethyl group to a halomethyl group may be achieved by reacting the compound containing the hydroxymethyl group with a halogenating agent in an inert solvent. Halogenating agents capable of converting hydroxy groups to halogen atoms are well-known in the art and any such agent may be employed in the present invention. Examples include: free halogens, such as bromine or iodine, or alkyl, particularly methyl, halides, such as methyl iodide, in the presence of a phosphorous compound (such as triphenylphosphine, triphenyl phosphite, trimethyl phosphite or triethyl phosphite); a carbon tetrahalide, such as carbon tetrachloride or carbon tetrabromide, in the presence of triphenylphosphine; a phosphorus halide, such as phosphorus trichloride, phosphorus tribromide, phosphorus triiodide or phosphorus pentachloride; or a sulfur halide, such as thionyl chloride or thionyl bromide; of these, we prefer a combination of bromine or iodine with triphenylphosphine. The solvent employed for this reaction is not critical, provided that it has no adverse effect upon the reaction. Suitable solvents include, for example: aromatic hydrocarbons, such as benzene, toluene or xylene; ethers, such as diethyl ether, tetrahydrofuran or dioxane; halogenated hydrocarbons, such as methylene chloride or chloroform; amides, such as dimethylformamide or dimethylacetamide; sulfoxides, such as dimethyl sulfoxide; or a mixture of any two or more thereof. When a combination of a halogen with a phosphorus compound is employed as a halogenating agent, a mixture of one or more of the above solvents with an organic base (such as pyridine, collidine or lutidine) may be preferable. The reaction can be effected over a wide range of temperatures, for example from 0° C. to 60° C. The time required for the reaction will vary, depending upon many factors, including the nature of the reagents and the reaction temperature, but a period of from 10 minutes to 3 days will normally suffice.

Halogenation of the hydroxy compound may also be carried out by treating the hydroxy compound with a sulfonyl halide, such as methanesulfonyl chloride, benzenesulfonyl chloride or p-toluenesulfonyl chloride in the presence of an organic base at about room temperature, to afford a sulfonyloxy compound, which is then treated with an alkali metal halide (such as lithium iodide, sodium bromide or sodium iodide) in an inert solvent (such as diethyl ether, tetrahydrofuran, methylene chloride or chloroform) at about room temperature for 1-10 hours. The corresponding halide (commonly chloride) may be produced during the sulfonyloxylation reaction, which forms the first part of this alternative halogenation process, without the subsequent treatment with an alkyl halide, depending upon the precise reaction conditions employed.

If desired, the halide thus obtained may be converted to another halide by conventional means. For example, the fluoro compound may be obtained by reacting the corresponding chloro compound or bromo compound with potassium fluoride, if necessary in the presence of a crown ether, such as 12-crown-4 or 15-crown-5, in a suitable solvent, such as ethylene glycol. Alternatively, reaction of the chloro compound with sodium iodide will give the corresponding iodo compound, whilst reaction of the iodo compound with t-butyldimethylsilyl chloride will give the corresponding chloro compound.

A halogen compound, which may have been prepared as described above, may then be reacted with an anion in an inert solvent, to give a corresponding compound where $R^1$ represents a carboxyalkyl group, an alkoxyalkyl group or an alkoxycarbonylalkyl group. Suitable anions include: carbanions, which can be produced from an aliphatic (commonly lower aliphatic, e.g. $C_2$–$C_6$) acid derivative, such as methyl isobutyrate, sodium isobutyrate, methyl 2-ethylbutyrate, methyl propionate or ethyl acetate; or alkoxyanions, which can be produced from an alcohol (which may optionally have an alkylamino or a dialkylamino substituent in which the or each alkyl part is $C_1$–$C_6$ alkyl), for example methanol, ethanol, propanol, 2-dimethylaminoethanol or 2-diethylaminoethanol.

The anion may be prepared by treating the aliphatic acid derivative or the alcohol with a base. Suitable bases include: organic lithium compounds, such as methyllithium, butyllithium, t-butyllithium or phenyllithium; dialkylaminolithium compounds, such as diisopropylaminolithium, dicyclohexylaminolithium or isopropylcyclohexylaminolithium; and alkali metal hydrides, such as lithium hydride, sodium hydride or potassium hydride; of these, the organic lithium compound or the dialkylaminolithium compound is preferred for the formation of a carbanion, whilst an alkali metal hydride is preferred for the formation of the alkoxyanion.

The reaction is preferably effected in the presence of an inert solvent, the nature of which is not critical, provided that it has no adverse effect upon the reaction. Suitable solvents include: ethers, such as diethyl ether, tetrahydrofuran or dioxane; and amides, such as dimethylformamide or dimethylacetamide; we prefer to employ an ether for the reaction to produce the carbanion and an amide for the reaction to produce the alkoxyanion.

Formation of the anion is preferably carried out at a relatively low temperature, for example from −78° C. to about room temperature, whilst reaction of the anion with the halogen compound, which may take place over a wide range of temperatures, is preferably effected at a temperature in the range from 0° C. to 60° C. The time required for each of these reactions would vary, depending upon the nature of the reagents and the reaction temperature, but a period of from 30 minutes to 2 hours will normally suffice for formation of the anion, whilst a period of from 1 to 24 hours will normally suffice for reaction of the anion with the halogen compound.

By treating the reaction mixture with a base in the course of this reaction, it is possible to convert the haloalkyl compound to an alkenyl compound.

Conversion of the ring sulfur atom to a sulfoxide or sulfone group may be effected by oxidizing the corresponding compound with a suitable oxidizing agent, preferably in the presence of an inert solvent. A wide range of oxidizing agents can be employed, for example, hydrogen peroxide or an organic peracid, such as peracetic acid, perbenzoic acid or m-chloroperbenzoic acid.

The nature of the solvent employed is not critical, provided that it has no adverse effect on the reaction. Water is the preferred solvent if hydrogen peroxide is used as the oxidizing agent, whilst preferred solvents for use with organic peracids include: ethers, such as diethyl ether, tetrahydrofuran or dioxane; aromatic hydrocarbons, such as benzene, toluene or xylene; and halogenated hydrocarbons, such as chloroform, methylene chloride or 1,2-dichloroethane.

To convert the sulfur atom to a sulfoxide group, an equimolar amount of the oxidizing agent is used, whereas, to convert it to a sulfone group, 2 moles or more of oxidizing agent are used for each mole of benzoxathiole compound.

Although the reaction temperature is not particularly critical, we generally find it convenient to carry out the reaction to form a sulfoxide at about room temperature, although a somewhat higher temperature (perhaps in the range of from room temperature to 50° C.) is preferably used to produce the sulfone. The time required for these reactions will vary depending upon many factors, including the nature of the reagents, the reaction temperature and the desired product, but a period of from 30 minutes to 5 hours will normally suffice.

Where a hydroxy group in the benzoxathiole compound is to be protected, the reaction to form the protecting group may be carried out by conventional means, the precise details depending upon the exact nature of the protecting group. For example, if the protecting group is an aliphatic or aromatic acyl group, an α-alkoxyalkyl group, a silyl group or an aralkyl group, the protecting reaction is achieved by reacting the benzoxathiole compound with the corresponding halide either in the presence of a base or after treatment with a base; suitable bases include, for example, triethylamine, pyridine, imidazole and sodium hydride. If the protecting group is an α-alkoxyalkyl group having a total of from 2 to 4 carbon atoms or a cyclic ether group, introduction of the protecting group may be effected by reacting the benzoxathiole compound with the corresponding vinyl ether compound (for example methyl vinyl ether, ethyl vinyl ether, dihydrofuran or dihydropyran) in the presence of an acid, such as methanesulfonic acid, p-toluenesulfonic acid or hydrochloric acid.

After completion of the above reactions, each desired product may be recovered from the reaction mixture by conventional means, the precise recovery technique depending upon the nature of the reaction mixture from which the compound is to be recovered. For example, one suitable recovery technique comprises: pouring the reaction mixture into ice-water; if necessary, neutralizing the resulting solution and/or filtering off any insolubles; extracting the product into a water-immiscible organic solvent; and then distilling the solvent from the extract, to give the desired product. If necessary, this product may be further purified by conventional means, for example recrystallization or the various chromotography techniques, such as column chromatography.

Method B

In this reaction, a compound of formula (Ib), that is to say a compound of formula (I) in which $R^2$ represents a $C_1-C_6$ alkyl group or a $C_3$ or $C_4$ alkenyl group, is prepared as illustrated in the following reaction scheme:

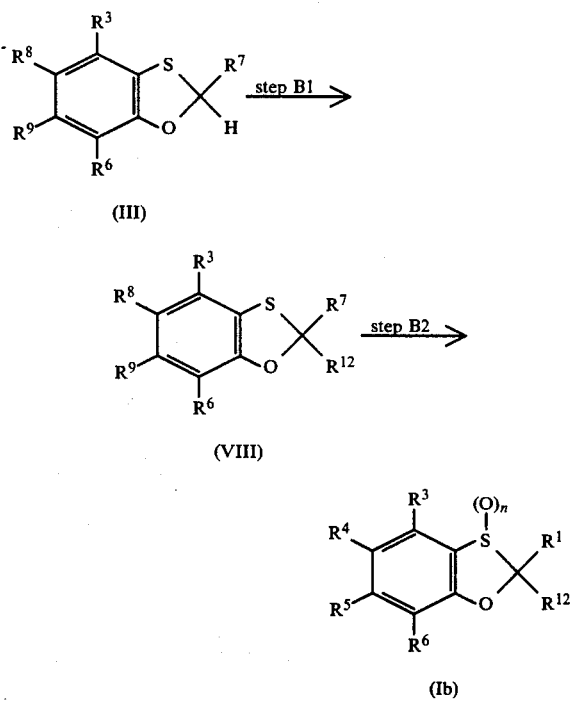

In the above formulae, $R^1$, $R^3$, $R^4$, $R^5$, $R^6$, $R^7$, $R^8$, $R^9$ and n are all as previously defined, whilst $R^{12}$ represents a $C_1-C_6$ alkyl group or a $C_3$ or $C_4$ alkenyl group.

In step B1 of this Method, a compound of formula (VIII) is prepared by converting a compound of formula (III) (which may have been prepared as described in Method A) to a carbanion by treating the compound of formula (III) with a base in an inert solvent, and then reacting the carbanion with a compound of formula (XI):

$$R^{12}-Y \qquad (XI)$$

(wherein: $R^{12}$ is as defined above; and Y represents a halogen atom, for example chlorine, bromine or iodine, or a sulfonyloxy group, for example a methanesulfonyloxy, ethanesulfonyloxy, benzenesulfonyloxy or p-toluenesulfonyloxy group). This reaction proceeds most effectively if $R^7$ represents an optionally substituted aryl group, in which any hydroxy group has been protected. The base used for this reaction is the same as those used in the corresponding reaction described in step A5 of Method A.

The nature of the solvent employed for this reaction is not critical, provided that it has no adverse effect upon the reaction. Suitable solvents include: aliphatic hydrocarbons, such as hexane or pentane; aromatic hydrocarbons, such as benzene, toluene or xylene; and ethers, such as diethyl ether, tetrahydrofuran or dioxane; of these, diethyl ether or tetrahydrofuran is particularly preferred.

The formation of the carbanion is preferably effected at a relatively low temperature, e.g. from $-100°$ C. to $0°$ C., more preferably from $-80°$ C. to $-30°$ C. The reaction of the carbanion with the halogeno or sulfonyl compound of formula (XI) may be carried out over a wide temperature range, for example from $-80°$ C. to $+50°$ C., more preferably from $-60°$ C. to about room temperature. The time required for each of these reactions may vary depending upon many factors, including the nature of the reagents and the reaction temperature; however, a period of from 10 minutes to 2 hours will normally suffice for preparation of the carbanion, whilst a period of from 30 minutes to 5 hours will normally suffice for reaction with the companion of formula (XI).

The desired product, the compund of formula (VIII), may be recovered from the reaction mixture by conventional means. For example, one suitable recovery technique comprises: pouring the reaction mixture into ice-water; extracting the product with a water-immiscible organic solvent; and then distilling the solvent from the extract, to give the desired product. If necessary, the product may be further purified by conventional means, for example recrystallization or the various chromatography techniques, such as column chromatography.

Step B2 is optional and includes all of the optional reactions described in relation to step A5, all of which may be carried out in the same way as described in Step A5.

Method C

In this Method, compounds of formula (Ic), that is to say compounds of formula (I) in which n is 0, may be prepared directly from a thiol compound of formula (IX), as illustrated in the following reaction:

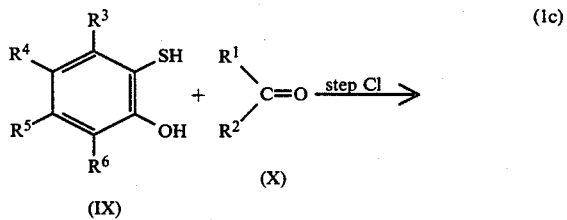

In the above formulae, $R^1$, $R^2$, $R^3$, $R^4$, $R^5$ and $R^6$ are as defined above.

Step C1 of this reaction may be achieved by reacting the compound of formula (IX) with a carbonyl compound of formula (X), in the presence of an acid and of a dehydrating agent, and in an inert solvent.

The carbonyl compound of formula (X) is preferably a ketone, in which neither $R^1$ nor $R^2$ represents a hydrogen atom, and is more preferably a dialkyl ketone in which both alkyl groups have from 1 to 6 carbon atoms, for example acetone, diethyl ketone or methyl propyl ketone.

Examples of acids which may be employed in this reaction include: mineral acids, such as hydrochloric acid, nitric acid or sulfuric acid; organic carboxylic acids, such as acetic acid, trifluoroacetic acid, trichloroacetic acid, propionic acid or benzoic acid; and sulfonic acids, such as methanesulfonic acid, ethanesulfonic acid, benzenesulfonic acid or p-toluenesulfonic acid; of these, we prefer trifluoroacetic acid, benzenesulfonic acid or p-toluenesulfonic acid. Suitable dehydrating agents incude Molecular Sieves 3A or 4A.

The nature of the solvent employed is not critical, provided that it has no adverse effect upon the reaction. Suitable solvents include: ethers, such as diethyl ether or tetrahydrofuran; and aromatic hydrocarbons, such as benzene, toluene or xylene. However, more preferably an excess of the carbonyl compound of formula (X) is employed and this serves as the solvent.

The reaction will take place over a very wide range of temperatures, and the precise temperature chosen is not critical to the reaction. A suitable temperature would be within the range from $0°$ C. to $200°$ C., more preferably from $50°$ C. to $150°$ C. The time required for the reaction will vary depending upon many factors, including the nature of the reagents and the reaction temperature; however, a period of from 30 minutes to 12 hours will normally suffice. The reaction is preferably carried out in an atmosphere of an inert gas (such as nitrogen or argon) in order to control side reactions.

The desired product of formula (Ic) may be recovered from the reaction mixture by conventional means. For example one suitable recovery technique comprises: distilling off the solvent; adding a weakly basic aqueous solution to the residue; extracting the desired compound with a water-immiscible organic solvent; and then distilling the solvent from the extract, to leave the desired compound. If necessary, the product may be further purified by such conventional means as recrystallization or the various chromatography techniques, such as column chromatography.

If necessary, the compound of formula (Ic) may be subjected to one or more of the reactions heretofore described in relation to step A5 of Method A; in particular, if the process of step C1 results in removal of any hydroxy-protecting group in the compound, a protecting group may be reinstated by conventional means.

Method D

This is an alternative method for the preparation of a compound of formula (Ic) from a thiol compound of formula (IX) and is summarized by the following reaction:

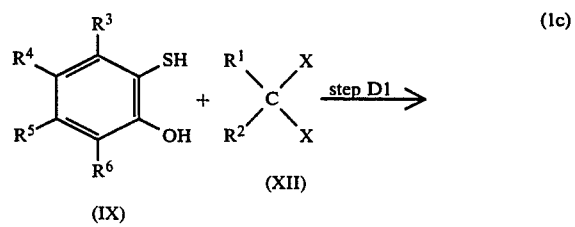

-continued

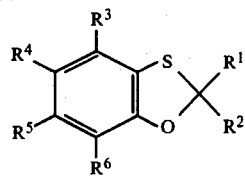

In the above formulae, $R^1$, $R^2$, $R^3$, $R^4$, $R^5$, $R^6$ and X are as defined above.

In this reaction, step D1 consists of reacting the compound of formula (IX) with a dihalo compound of formula (XII) in the presence of a base and of a phase transfer catalyst, and in a solvent.

This reaction is particularly effective for those compounds of formula (XII) in which $R^1$ and $R^2$ are the same or different and each represents a hydrogen atom or a $C_1-C_6$ alkyl group, more preferably a hydrogen atom, or a methyl or ethyl group.

Examples of bases which may be employed in this reaction include alkali metal carbonates (such as sodium carbonate or potassium carbonate) and alkali metal bicarbonates (such as sodium bicarbonate or potassium bicarbonate), preferably an alkali metal bicarbonate.

Examples of suitable phase tranfer catalysts include tetraalkylammonium halides, such as trioctylmethylammonium chloride, tri(decyl)methylammonium bromide and tetraoctylammonium iodide, preferably trioctylmethylammonium halides. If necessary, the reaction may be carried out in an atmosphere of an inert gas, for example nitrogen.

The solvent employed in the reaction is not particularly critical, provided that it does not adversely affect the reaction. Examples of suitable solvents include: water; alcohols, such as methanol or ethanol; aliphatic hydrocarbons, such as hexane, heptane or octane; aromatic hydrocarbons, such as benzene, toluene or xylene; ethers, such as diethyl ether, tetrahydrofuran of dioxane; or, and preferably, a mixture of an excess of the dihalo compound of formula (XII) with water.

The reaction may be effected over a wide range of temperatures, but preferably at a temperature from 20° C. to 130° C., more preferably from 80° C. to 110° C. The time required for the reaction will vary depending upon many factors, including the nature of the reagents and the reaction temperature, but a period of from 2 to 20 hours, more commonly from 5 to 12 hours, will normally suffice.

After completion of the reaction, the desired product of formula (Ic) may be recovered from the reaction mixture by conventional means, for example by distilling off the solvent; if necessary, the residue may be purified by conventional means, such as recrystallization or the various chromatography techniques, such as column chromatography.

If required, the compound of formula (Ic) may be subjected to any one or more of those reactions described heretofore in step A5 of Method A: In particular, if a hydroxy-protecting group has been removed in the course of the reaction of step D1, it may be reinstated by conventional means.

As already described, the compounds of the invention have a variety of valuable activities, which allow them to be used for the treatment of circulatory disorders (particularly for the improvement of serum lipid levels and as anti-thrombotic agents) or for the treatment of allergies. The compounds of the invention may be administered by various routes, but preferably orally, externally (e.g., topically) or parenterally (particularly intramuscularly or intravenously) and more preferably orally. The compounds may be formulated in a variety of conventional formulations suited to the intended mode of administration. For example, for oral administration, the compound of the invention may be formulated as tablets, capsules, granules, powders, syrups or inhalents. For parenteral administration, the compound is preferably formulated in a suitable pyrogen-free liquid vehicle. For topical administration, the compound is preferably formulated in an ointment or cream. The dosage will vary depending upon the age and symptoms of the patient and the route of administration, but for an adult human, a suitable daily dosage would be from 1 to 3,000 mg, more preferably from 15 to 1,000 mg, which could be administered in a single dose or in divided doses.

The invention is further illustrated by the following Examples. In these Examples, Examples 1 to 21 illustrate the preparation of various of the starting materials employed in the processes of the invention, Examples 22 to 98 illustrate the preparation of various compounds of the present invention and Examples 99 and 100 illustrate the therapeutic activities in recognized test systems.

EXAMPLE 1

3,3',5,5',6,6'-Hexamethyl-2,2'-dithiobishydroquinone
and
3,3',5,5',6,6'-hexamethyl-2,2'-trithiobishydroquinone (a) Preparation of dithio compound using a thiol compound A mixture of 7.5 g of 2-mercapto-3,5,6-trimethylhydroquinone and 100 ml of diethyl ether was allowed to stand in the air at room temperature for 1 day. The solvent was then evaporated off and the residue thus obtained was recrystallized from tetrahydrofuran, to give 5.5 g of the dithio title compound as vivid yellow crystals, melting at 227°–230° C.

Infrared Absorption Spectrum (Nujol-trade markmull): $v_{max}$ cm$^{-1}$: 3380, 3425.

(b) Preparation using sulfur monochloride 30 g of trimethylhydroquinone were dissolved in 1.2 liter of anhydrous acetonitrile. 1.4 g of iron powder was then added to the solution. The solution was then cooled to $-30°$ C., and a solution of 13.3 g of sulfur monochloride in 50 ml of anhydrous acetonitrile was added dropwise to the mixture under a stream of nitrogen. The reaction temperature was then allowed to rise to room temperature and the reaction mixture was stirred for 4 hours. At the end of this time, the precipitate produced was filtered off and the filtrate was condensed. The residue was purified by silica gel column chromatography. From the fraction eluted with a 10:0.5 by volume mixture of benzene and tetrahydrofuran was obtained 1.0 g of the dithio title compound, which had the same melting point and infrared absorption spectrum as did the product of Example 1(a).

From the precipitate which had been filtered off and was in the form of crystals were obtained 17.0 g of 3,3',5,5',6,6'-hexamethyl-2,2'-trithiobishydroquinone, melting at 190°–193° C. (with decomposition).

Infrared Absorption Spectrum (Nujol mull) $v_{max}$ cm$^{-1}$: 3400.

EXAMPLE 2

5,5',6,6'-Tetramethoxy-3,3'-dimethyl-2,2'-dithiobishydroquinone and
5,5',6,6'-tetramethoxy-3,3'-dimethyl-2,2'-trithiobishydroquinone The procedures for reaction and treatment of the reaction mixture described in Example 1(b) were repeated, to give the dithio and trithio compounds in crude form from 2,3-dimethoxy-5-methylhydroquinone and sulfur monochloride, and these products were purified by silica gel column chromatography eluted with a 9:1 by volume mixture of benzene and ethyl acetate, to give the pure trithio compound (in an amorphous state) from the fractions first eluted, followed by the pure crystalline dithio compound from subsequent fractions.

Dithio compound

Melting at: 153°–155° C.

Silica gel thin layer chromatography: Rf value=0.46 (Developing solvent, benzene:ethyl acetate=6:4 by volume).

Trithio compound

Silica gel thin layer chromatography: Rf value=0.53 (Developing solvent, benzene:ethyl acetate=6:4 by volume).

EXAMPLE 3

3,3',6,6'-Tetramethyl-2,2'-dithiobis(1,4,5-benzenetriol)
and
3,3',6,6'-tetramethyl-2,2'-trithiobis(1,4,5-benzenetriol)

The procedures for reaction and treatment of the reaction mixture described in Example 1(b) were repeated, to give the dithio and trithio compounds in crude form from 3,6-dimethyl-1,2,4-benzenetriol and sulfur monochloride, and these products were purified by silica gel column chromatography eluted with an 8:2 by volume mixture of benzene and ethyl acetate, to give the pure trithio compound (in an amorphous state) from the fractions first eluted, followed by the pure crystalline dithio compound from subsequent fractions.

Dithio compound

Melting at 192°–194° C.

Silica gel thin layer chromatography: Rf value=0.43 (Developing solvent, benzene:ethyl acetate=6:4 by volume).

Trithio compound

Silica gel thin layer chromatography: Rf value=0.50 (Developing solvent, benzene:ethyl acetate=6:4 by volume).

EXAMPLE 4

3,3',5,5',6,6'-Hexamethyl-2,2'-trithiobis(1,4-phenylene) tetraacetate 10 g of 3,3',5,5',6,6'-hexamethyl-2,2'-trithiobishydroquinone, prepared as described in Example 1(b), were dissolved in 70 ml of pyridine. To the solution were added 30 g of acetic anhydride, and the mixture was stirred for 24 hours at room temperature. At the end of this time, the reaction mixture was poured into water and the resulting precipitate was taken up in chloroform. The chloroform phase was separated, washed with water and dried over anhydrous sodium sulfate. The solvent was distilled off and the residue was recrystallized from benzene to give 5.7 g of the title compound, melting at 187°–190° C.

Infrared Absorption Spectrum (Nujol mull) $\nu_{max}$ cm$^{-1}$: 1760.

Mass spectrum (m/e): 566 (M+).

EXAMPLE 5

3,3',5,5',6,6'-Hexamethyl-2,2'-trithiobis(1,4-phenylene) tetrabutyrate

The title compound, melting at 153°–155° C., was obtained by following the procedures described in Example 4, but using 3,3',5,5',6,6'-hexamethyl-2,2'-trithiobishydroquinone, prepared as described in Example 1(b), and butyryl chloride.

Infrared Absorption Spectrum (Nujol mull) $\nu_{max}$ cm$^{-1}$: 1750.

Mass spectrum (m/e): 678 (M+).

EXAMPLES 6–19

By following the procedures of Example 4 or Example 5, but using the appropriate mercapto compound and the acylating agents described below, the following compounds were prepared:

EXAMPLE 6

The process of Example 5 was employed, with propionyl chloride as the acylating agent, to prepare 3,3',5,5',6,6'-hexamethyl-2,2'-trithiobis(1,4-phenylene)-tetrapropionate.

Silica gel thin layer chromatography: Rf value=0.39 (Developing solvent, benzene:tetrahydrofuran=20:1 by volume).

Infrared Absorption Spectrum (Nujol mull) $\nu_{max}$ cm$^{-1}$: 1750.

EXAMPLE 7

The process of Example 5 was employed, with isobutyryl chloride as the acylating agent, to prepare 3,3',5,5',6,6'-hexamethyl-2,2'-trithiobis(1,4-phenylene)-tetraisobutyrate.

Silica gel thin layer chromatography: Rf value=0.13 (Developing solvent, benzene).

Infrared Absorption Spectrum (Nujol mull) $\nu_{max}$ cm$^{-1}$: 1750.

EXAMPLE 8

The process of Example 4 was employed, with valeric anhydride as the acylating agent, to prepare 3,3',5,5',6,6'-hexamethyl-2,2'-trithiobis(1,4-phenylene)-tetravalerate.

Silica gel thin layer chromatography: Rf value=0.73 (Developing solvent, benzene:tetrahydrofuran=20:1 by volume).

EXAMPLE 9

The process of Example 5 was employed, with heptanoyl chloride as the acylating agent, to prepare 3,3',5,5',6,6'-hexamethyl-2,2'-trithiobis(1,4-phenylene)-tetraheptanoate.

Silica gel thin layer chromatography: Rf value=0.30 (Developing solvent, benzene).

Infrared Absorption Spectrum (Nujol mull) $\nu_{max}$ cm$^{-1}$: 1750.

EXAMPLE 10

The process of Example 5 was employed, with octanoyl chloride as the acylating agent, to prepare 3,3′,5,5′,6,6′-hexamethyl-2,2′-trithiobis(1,4-phenylene)-tetraoctanoate.

Silica gel thin layer chromatography: Rf value=0.31 (Developing solvent, benzene).

EXAMPLE 11

The process of Example 5 was employed, with arachidyl chloride (systematic name: eicosanoyl chloride) as the acylating agent, to prepare 3,3′,5,5′,6,6′-hexamethyl-2,2′-trithiobis(1,4-phenylene)tetraarachidate.

Silica gel thin layer chromatography: Rf value=0.56 (Developing solvent, benzene).

Infrared Absorption Spectrum (Nujol mull) $\nu_{max}$ cm$^{-1}$: 1755.

EXAMPLE 12

The process of Example 5 was employed, with 3,7,11,15-tetramethylhexadecanoyl chloride as the acylating agent, to prepare 3,3′,5,5′,6,6′-hexamethyl-2,2′-trithiobis(1,4-phenylene) tetrakis(3,7,11,15-tetramethylhexadecanoate).

Silica gel thin layer chromatography: Rf value=0.53 (Developing solvent, benzene).

EXAMPLE 13

The process of Example 5 was employed, with 3-methoxycarbonylpropionyl chloride as the acylating agent, to prepare 3,3′,5,5′,6,6′-hexamethyl-2,2′-trithiobis-(1,4-phenylene) tetrakis(3-methoxycarbonylpropionate).

Silica gel thin layer chromatography: Rf value=0.40 (Developing solvent, benzene:ethyl acetate=4:1 by volume).

Infrared Absorption Spectrum (liquid film) $\nu_{max}$ cm$^{-1}$: 1760, 1740.

EXAMPLE 14

The process of Example 5 was employed, with 3-ethoxycarbonylpropionyl chloride as the acylating agent, to prepare 3,3′,5,5′,6,6′-hexamethyl-2,2′-trithiobis-(1,4-phenylene) tetrakis(3-ethoxycarbonylpropionate).

Silica gel thin layer chromatography: Rf value=0.41 (Developing solvent, benzene:ethyl acetate=4:1 by volume).

Infrared Absorption Spectrum (liquid film) $\nu_{max}$ cm$^{-1}$: 1760, 1740.

EXAMPLE 15

The process of Example 5 was employed, with 3-butoxycarbonylpropionyl chloride as the acylating agent, to prepared 3,3′,5,5′,6,6′-hexamethyl-2,2′-trithiobis-(1,4-phenylene) tetrakis(3-butoxycarbonylpropionate).

Silica gel thin layer chromatography: Rf value=0.44 (Developing solvent, benzene:tetrahydrofuran=20:1 by volume).

Infrared Absorption Spectrum (liquid film) $\nu_{max}$ cm$^{-1}$: 1760, 1740.

EXAMPLE 16

The process of Example 5 was employed, with benzoyl chloride as the acrylating agent, to prepare 3,3′,5,5′,6,6′-hexamethyl-2,2′-trithiobis(1,4-phenylene)-tetrabenzoate, melting at 230°–232° C.

Infrared Absorption Spectrum (Nujol mull) $\nu_{max}$ cm$^{-1}$: 1740.

EXAMPLE 17

The process of Example 5 was employed, with o-acetoxybenzoyl chloride as the acylating agent, to prepare 3,3′,5,5′,6,6′-hexamethyl-2,2′-trithiobis-(1,4-phenylene) tetra(o-acetoxybenzoate).

Silica gel thin layer chromatography: Rf value=0.24 (Developing solvent, benzene:ethyl acetate=10:1 by volume).

Infrared Absorption Spectrum (Nujol mull) $\nu_{max}$ cm$^{-1}$: 1770, 1740.

EXAMPLE 18

The process of Example 5 was employed, with p-methoxycarbonylbenzoyl chloride as the acylating agent, to prepare 3,3′,5,5′,6,6′-hexamethyl-2,2′-trithiobis-(1,4-phenylene) tetra(p-methoxycarbonylbenzoate), melting at 275°–278° C.

Infrared Absorption Spectrum (Nujol mull) $\nu_{max}$ cm$^{-1}$: 1730.

EXAMPLE 19

The process of Example 5 was employed, with p-chlorobenzoyl chloride as the acylating agent, to prepare 3,3′,5,5′,6,6′-hexamethyl-2,2′-trithiobis-(1,4-phenylene) tetra(p-chlorobenzoate), melting at 268°–273° C.

Infrared Absorption Spectrum (Nujol mull) $\nu_{max}$ cm$^{-1}$: 1735.

EXAMPLE 20

5,5′,6,6′-Tetramethoxy-3,3′-dimethyl-2,2′-dithiobis(1,4-phenylene)tetraacetate

The procedures for reaction and treatment of the reaction mixture described in Example 4 were repeated, but using 5,5′,6,6′-tetramethoxy-3,3′-dimethyl-2,2′-dithiobishydroquinone, prepared as described in Example 2, and acetic anhydride, followed by purification by silica gel column chromatography eluted with a 9:1 by volume mixture of benzene and ethyl acetate, to give the title compound.

Silica gel thin layer chromatography: Rf value=0.45 (Developing solvent, benzene:ethyl acetate=8:2 by volume).

EXAMPLE 21

3,3′,6,6′-Tetramethyl-2,2′-dithiobis(1,4,5-benzenetrilyl)-hexaacetate

The procedures for reaction and treatment of the reaction mixture described in Example 4 were repeated, but using 3,3′,6,6′-tetramethyl-2,2′-dithiobis(1,4,5-benzenetriol), prepared as described in Example 3, and acetic anhydride, followed by purification by silica gel column chromatography eluted with an 8:2 by volume mixture of benzene and ethyl acetate, to give the title compound.

Silica gel thin layer chromatography: Rf value=0.59 (Developing solvent, benzene: ethyl acetate=6:4 by volume).

Infrared Absorption Spectrum (Nujol mull) $\nu_{max}$ cm$^{-1}$: 1780.

EXAMPLE 22

5-Acetoxy-2,4,6,7-tetramethyl-1,3-benzoxathiole (a) Preparation using trithio compound and zinc powder 6.3 g of 3,3′,5,5′,6,6′-hexamethyl-2,2′-trithiobis(1,4-phenylene)tetraacetate, prepared as described in Example 4, were dissolved in 120 ml of acetic acid. To the solution were added 13 g of zinc powder, and the mixture was heated under reflux for 10 hours under a stream of nitrogen. At the end of this time, the insolubles produced were filtered off, and the resulting acetic acid solution was condensed to give a crude oil, which was dissolved in benzene. The benzene solution was washed with water and dried over anhydrous sodium sulfate. The solvent was distilled off and the residue thus obtained was purified by silica gel column chromatography. From the fraction eluted with benzene were obtained 4.4 g of the title compound, and this was recrystallized from hexane to give 3.5 g of a pure product, melting at 72°-74° C.

Infrared Absorption Spectrum (Nujol mull) $\nu_{max}$ cm$^{-1}$: 1750.

Mass Spectrum (m/e): 252 (M+).

(b) Preparation using trithio compound and iron powder

The reaction, treatment and purification of the reaction mixture described in Example 22(a) were repeated, but using iron powder in place of zinc powder, to give the title compound, whose melting point and infrared absorption spectrum were identical with those of the product obtained as described in Example 22(a)

(c) Preparation using dithio compound and zinc powder

The reaction, treatment and purification of the reaction mixture described in Example 22(a) were repeated, but using 3,3′,5,5′,6,6′-hexamethyl-2,2′-dithiobis(1,4-phenylene)tetraacetate instead of 3,3′,5,5′,6,6′-hexamethyl-2,2′-trithiobis-(1,4-phenylene)tetraacetate, to give the title compound. The melting point and infrared absorption spectrum of this product were identical with those of the product obtained as described in Example 22(a).

EXAMPLES 23-37

The following compounds were prepared by the method described in Example 22(a), but employing appropriate trithiobisphenylene esters as starting materials.

EXAMPLE 23

2-ethyl-4,6,7-trimethyl-5-propionyloxy-1,3-benzoxathiole.

Silica gel thin layer chromatography: Rf value=0.46 (Developing solvent, benzene:hexane=4:1 by volume).

Infrared Absorption Spectrum (liquid film) $\nu_{max}$ cm$^{-1}$: 1760.

Mass Spectrum (m/e): 280 (M+).

EXAMPLE 24

5-butyryloxy-4,6,7-trimethyl-2-propyl-1,3-benzoxathiole.

Silica gel thin layer chromatography: Rf value=0.47 (Developing solvent, benzene:cyclohexane=4:1 by volume).

Infrared Absorption Spectrum (liquid film) $\nu_{max}$ cm$^{-1}$: 1760.

Mass spectrum (m/e): 308 (M+).

EXAMPLE 25

5-isobutyryloxy-2-isopropyl-4,6,7-trimethyl-1,3-benzoxathiole.

Silica gel thin layer chromatography: Rf value=0.47 (Developing solvent, benzene:cyclohexane=4:1 by volume).

Infrared Absorption Spectrum (liquid film) $\nu_{max}$ cm$^{-1}$: 1760.

Mass spectrum (m/e): 308 (M+).

EXAMPLE 26

2-butyl-4,6,7-trimethyl-5-valeryloxy-1,3-benzoxathiole.

Silica gel thin layer chromatography: Rf value=0.60 (Developing solvent, benzene:hexane=4:1 by volume).

Infrared Absorption Spectrum (liquid film) $\nu_{max}$ cm$^{-1}$: 1760.

Mass spectrum (m/e): 336 (M+).

EXAMPLE 27

5-heptanoyloxy-2-hexyl-4,6,7-trimethyl-1,3-benzoxathiole.

Silica gel thin layer chromatography: Rf value=0.71 (Developing solvent, benzene:hexane=4:1 by volume).

Infrared Absorption Spectrum (liquid film) $\nu_{max}$ cm$^{-1}$: 1760.

Mass spectrum (m/e): 392 (M+).

EXAMPLE 28

2-heptyl-4,6,7-trimethyl-5-octanoyloxy-1,3-benzoxathiole.

Silica gel thin layer chromatography: Rf value=0.80 (Developing solvent, benzene).

Infrared Absorption Spectrum (liquid film) $\nu_{max}$ cm$^{-1}$: 1760.

Mass spectrum (m/e): 420 (M+).

EXAMPLE 29

5-arachidyloxy-4,6,7-trimethyl-2-nonadecyl-1,3-benzoxathiole, melting at 80°-81° C.

Infrared Absorption Spectrum (Nujol mull) $\nu_{max}$ cm$^{-1}$: 1750.

Mass Spectrum (m/e): 756 (M+).

EXAMPLE 30

4,6,7-trimethyl-5-(3,7,11,15-tetramethylhexadecanoyloxy)-2-(2,6,10,14-tetramethylpentadecyl)-1,3-benzoxathiole.

Silica gel thin layer chromatography: Rf value=0.80 (Developing solvent, benzene:hexane=1:1 by volume).

Infrared Absorption Spectrum (liquid film) $\nu_{max}$ cm$^{-1}$: 1755.

Mass spectrum (m/e): 756 (M+).

EXAMPLE 31 methyl 3-[5-(3-methoxycarbonylpropionyloxy)-4,6,7-trimethyl-1,3-benzoxathiole-2-yl]priopionate.

Silica gel thin layer chromatography: Rf value=0.50 (Developing solvent, benzene:ethyl acetate=10:1 by volume).

Infrared Absorption Spectrum (Nujol mull) $\nu_{max}$ cm$^{-1}$: 1740 (shoulder), 1735.

Mass spectrum (m/e): 396 (M+).

EXAMPLE 32 ethyl 3-[5-(3-ethoxycarbonylpropionyloxy)-4,6,7-trimethyl-1,3-benzoxathiole-2-yl]propionate.

Silica gel thin layer chromatography: Rf value=0.53 (Developing solvent, benzene:ethyl acetate=10:1 by volume).

Infrared Absorption Spectrum (liquid film) $\nu_{max}$ cm$^{-1}$: 1760, 1740.

Mass spectrum (m/e): 424 (M+).

EXAMPLE 33 butyl 3-[5-(3-butoxycarbonylpropionyloxy)-4,6,7-trimethyl-1,3-benzoxathiole-2-yl]propionate.

Silica gel thin layer chromatography: Rf value=0.52 (Developing solvent, benzene:ethyl acetate=20:1 by volume)

Infrared Absorption Spectrum (liquid film) $\nu_{max}$ cm$^{-1}$: 1760, 1740.

Mass spectrum (m/e): 480 (M+).

EXAMPLE 34

5-benzoyloxy-4,6,7-trimethyl-2-phenyl-1,3-benzoxathiole, melting at 120°–124° C.

Infrared Absorption Spectrum (Nujol mull) $\nu_{max}$ cm$^{-1}$: 1740.

Mass spectrum (m/e): 376 (M+).

EXAMPLE 35

5-(o-acetoxybenzoyloxy)-2-(o-acetoxyphenyl)-4,6,7-trimethyl-1,3-benzoxathiole.

Silica gel thin layer chromatography: Rf value=0.46 (Developing solvent, benzene:ethyl acetate=20:1 by volume).

Infrared Absorption Spectrum (Nujol mull) $\nu_{max}$ cm$^{-1}$: 1770, 1740.

Mass spectrum (m/e): 492 (M+).

EXAMPLE 36 methyl 4-[5-(p-methoxycarbonylbenzoyloxy)-4,6,7-trimethyl-1,3-benzoxathiole-2-yl]benzoate, melting at 155°–160° C.

Infrared Absorption Spectrum (Nujol mull) $\nu_{max}$ cm$^{-1}$: 1735, 1730.

Mass spectrum (m/e): 492 (M+).

EXAMPLE 37

5-(p-chlorobenzoyloxy)-2-(p-chlorophenyl)-4,6,7-trimethyl-1,3-benzoxathiole.

Silica gel thin layer chromatography: Rf value=0.45 Developing solvent, benzene:cyclohexane=1:1 by volume).

Infrared Absorption Spectrum (Nujol mull) $\nu_{max}$ cm$^{-1}$: 1740.

Mass spectrum (m/e): 444 (M+).

EXAMPLE 38

5-Acetoxy-6,7-dimethoxy-2,4-dimethyl-1,3-benzoxathiole

The procedures for reaction and treatment of the reaction mixture described in Example 22(a) were repeated, but using a 1:3 by weight mixture of 5,5',6,6'-tetramethoxy-3,3'-dimethyl-2,2'-dithiobis(1,4-phenylene) tetraacetate and 5,5',6,6'-tetramethoxy-3,3'-dimethyl-2,2'-trithiobis(1,4-phenylene) tetraacetate (prepared as described in Example 20, but from an unseparated mixture of dithio and trithio compounds prepared as described in Example 2), after which the product was purified by silica gel column chromatography eluted with a 10:0.5 by volume mixture of benzene and ethyl acetate, to give the title compound.

Infrared Absorption Spectrum (liquid film) $\nu_{max}$ cm$^{-1}$: 1770.

Silica gel thin layer chromatography: Rf value=0.54 (Developing solvent, benzene:ethyl acetate=10:1 by volume).

Mass spectrum (m/e): 284 (M+).

EXAMPLE 39

5,6-Diacetoxy-2,4,7-trimethyl-1,3-benzoxathiole

The procedures for reaction and treatment of the reaction mixture described in Example 22(a) were repeated, but using an equimolar mixture of 3,3',6,6'-tetramethyl-2,2'-dithiobis(1,4,5-benzenetriyl)hexaacetate and 3,3',6,6'-tetramethyl-2,2'-trithiobis(1,4,5-benzenetriyl)hexaacetate, after which the product was purified by silica gel column chromatography eluted with a 10:0.5 by volume mixture of benzene and ethyl acetate, to give the title compound, melting at 82°–84° C.

Infrared Absorption Spectrum (Nujol mull) $\nu_{max}$ cm$^{-1}$: 1755.

Silica gel thin layer chromatography: Rf value=0.59 (Developing solvent, benzene:ethyl acetate=10:1 by volume).

Mass spectrum (m/e): 296 (M+).

EXAMPLE 40

5-Hydroxy-2,4,6,7-tetramethyl-1,3-benzoxathiole 2.9 g of 5-acetoxy-2,4,6,7-tetramethyl-1,3-benzoxathiole, prepared as described in Example 22, were dissolved in 30 ml of methanol, 1.3 g of sodium methoxide was added to the solution, and the mixture was allowed to react at room temperature for 3 hours. At the end of this time, the reaction mixture was poured into water and the solution was neutralized by adding acetic acid. The separated product was extracted with benzene and the extract was washed with water and dried over anhydrous sodium sulfate. The solvent was evaporated off. The crude product thus obtained was purified by silica gel column chromatography. From the fraction eluted with a 1:1 by volume mixture of hexane and benzene were obtained 2.0 g of the title compound, melting at 125°–127° C.

Infrared Absorption Spectrum (Nujol mull) $\nu_{max}$ cm$^{-1}$: 3330.

EXAMPLES 41–50

The following compounds were prepared by the method described in Example 40, but employing the appropriate 5-acyloxybenzoxathiole compound as starting material.

EXAMPLE 41

2-ethyl-5-hydroxy-4,6,7-trimethyl-1,3-benzoxathiole, melting at 85°–85.5° C.

Silica gel thin layer chromatography: Rf value=0.71 (Developing solvent, benzene).

Infrared Absorption Spectrum (Nujol mull) $\nu_{max}$ cm$^{-1}$: 3320.

Mass spectrum (m/e): 224 (M+).

EXAMPLE 42

5-hydroxy-4,6,7-trimethyl-2-propyl-1,3-benzoxathiole, melting at 72°–73° C.

Silica gel thin layer chromatography: RF value=0.49 (Developing solvent, benzene).

Infrared Absorption Spectrum (Nujol mull) $\nu_{max}$ cm$^{-1}$: 3300.

Mass spectrum (m/e): 238 (M+).

EXAMPLE 43

5-hydroxy-2-isopropyl-4,6,7-trimethyl-1,3-benzoxathiole.

Silica gel thin layer chromatography: Rf value=0.48 (Developing solvent, benzene).

Infrared Absorption Spectrum (Nujol mull) $\nu_{max}$ cm$^{-1}$: 3250.

Mass spectrum (m/e): 238 (M+).

EXAMPLE 44

2-butyl-5-hydroxy-4,6,7-trimethyl-1,3-benzoxathiole, melting at 73.5°–74.5° C.

Silica gel thin layer chromatography: RF value=0.48 (Developing solvent, benzene).

Infrared Absorption Spectrum (Nujol mull) $\nu_{max}$ cm$^{-1}$: 3200.

Mass spectrum (m/e): 252 (M+).

EXAMPLE 45

2-hexyl-5-hydroxy-4,6,7-trimethyl-1,3-benzoxathiole, melting at 76.5°–77.0° C.

Silica gel thin layer chromatography: Rf value=0.76 (Developing solvent, benzene).

Infrared Absorption Spectrum (Nujol mull) $\nu_{max}$ cm$^{-1}$: 3200.

Mass spectrum (m/e): 280 (M+).

EXAMPLE 46

2-heptyl-5-hydroxy-4,6,7-trimethyl-1,3-benzoxathiole, melting at 76°–76.5° C.

Silica gel thin layer chromatography: Rf value=0.51 (Developing solvent, benzene).

Infrared Absorption Spectrum (Nujol mull) $\nu_{max}$ cm$^{-1}$: 3200.

Mass spectrum (m/e): 294 (M+).

EXAMPLE 47

In this Example, the base used was sodium hydroxide (in place of sodium methoxide) and the solvent was a 1:1 by volume mixture of methanol and tetrahydrofuran (in place of methanol alone), to give:

5-hydroxy-4,6,7-trimethyl-2-nonadecyl-1,3-benzoxathiole, melting at 96°–96.5° C.

Silica gel thin layer chromatography: Rf value=0.61 (Developing solvent, benzene).

Infrared Absorption Spectrum (Nujol mull) $\nu_{max}$ cm$^{-1}$: 3200.

Mass spectrum (m/e): 462 (M+).

EXAMPLE 48

5-hydroxy-4,6,7-trimethyl-2-(2,6,10,14-tetramethylpentadecyl)-1,3-benzoxathiole.

Silica gel thin layer chromatography: Rf value=0.61 (Developing solvent, benzene).

Infrared Absorption Spectrum (liquid film) $\nu_{max}$ cm$^{-1}$: 3200.

Mass spectrum (m/e): 462 (M+).

EXAMPLE 49

3-(5-hydroxy-4,6,7-trimethyl-1,3-benzoxathiole-2-yl)propionic acid, melting at 138°–140° C.

Silica gel thin layer chromatography: Rf value=0.13 (Developing solvent, benzene:ethyl acetate=4:1 by volume).

Infrared Absorption Spectrum (Nujol mull) $\nu_{max}$ cm$^{-1}$: 3450, 1720.

Mass spectrum (m/e): 268 (M+).

EXAMPLE 50

5-hydroxy-4,6,7-trimethyl-2-phenyl-1,3-benzoxathiole, melting at 129°–132° C.

Infrared Absorption Spectrum (Nujol mull) $\nu_{max}$ cm$^{-1}$: 3370.

Mass spectrum (m/e): 272 (M+).

EXAMPLE 51

5-Hydroxy-4,6,7-trimethyl-2-(2,6,10,14-tetramethylpentadecyl)-1,3-benzoxathiole

This is an alternative preparation to the compound described in Example 48, for preparing the same compound.

1.5 g of 4,6,7-trimethyl-5-(3,7,11,15-tetramethylhexadecanoyloxy)-2-(2,6,10,14-tetramethylpentadecyl)-1,3-benzoxathiole were dissolved in 15 ml of tetrahydrofuran, and 100 mg of lithium aluminum hydride were added to the solution under a stream of nitrogen and with ice-cooling. The mixture was allowed to react for 15 minutes, and then a solution of 0.8 g of acetic acid in 10 ml of tetrahydrofuran was added dropwise to the solution, whilst ice-cooling. The mixture was allowed to react for 1 hour at room temperature, and then the tetrahydrofuran was evaporated off under reduced pressure and ice-water was added to the residue thus obtained. The reaction mixture was extracted with hexane. The extract was washed with water and dried over anhydrous sodium sulfate. The solvent was evaporated off and the residue thus obtained was subjected to silica gel column chromatography. From the fraction eluted with a 1:2 by volume mixture of benzene and hexane was obtained 754 mg of the title compound, showing the same Rf value, infrared absorption spectrum and mass spectrum as did the product obtained as described in Example 48.

EXAMPLE 52

5-(o-Hydroxybenzoyloxy)-2-(o-hydroxyphenyl)-4,6,7-trimethyl-1,3-benzoxathiole

A mixture of 282 mg of 5-(o-acetoxybenzoyloxy)-2-(o-acetoxyphenyl)-4,6,7-trimethyl-1,3-benzoxathiole, 290 mg of potassium hydroxide and 3 ml of methanol was reacted at 10° C. for 12 hours. Subsequent treatment of the reaction mixture was conducted in the same manner as in Example 40. From the fraction eluted with a 50:1 by volume mixture of benzene and ethyl acetate from a silica gel chromatography column were obtained 110 mg of the title compound.

Silica gel thin layer chromatography: Rf value=0.12 (Developing solvent, benzene).

Infrared Absorption Spectrum (chloroform solution): $\nu_{max}$ cm$^{-1}$: 1675.

Mass spectrum (m/e): 408 (M+).

EXAMPLE 53

5-Hydroxy-2-(o-hydroxyphenyl)-4,6,7-trimethyl-1,3-benzoxathiole

A mixture of 700 mg of 5-(o-acetoxybenzoyloxy)-2-(o-acetoxyphenyl)-4,6,7-trimethyl-1,3-benzoxathiole, 0.5 g of sodium hydroxide and 10 ml of methanol was heated under reflux for 1.5 hours. Subsequent treatment and purification of the reaction mixture were conducted in the same manner as in Example 52. From the fraction eluted with a 50:1 by volume mixture of benzene and ethyl acetate were obtained 260 mg of the title compound, melting at 175°–176° C.

Infrared Absorption Spectrum (Nujol mull) $\nu_{max}$ cm$^{-1}$: 3520, 3360.

Mass spectrum (m/e): 288 (M+).

EXAMPLE 54

4-(5-Hydroxy-4,6,7-trimethyl-1,3-benzoxathiole-2-yl)benzoic acid

A mixture of 2.2 g of 5-(p-methoxycarbonylbenzoyloxy)-2-(p-methoxycarbonylphenyl)-4,6,7-trimethyl-1,3-benzoxathiole, 1.6 g of sodium hydroxide and 60 ml of methanol was heated under reflux for 3 hours. Subsequent treatment and purification of the reaction mixture were conducted in the same manner as described in Example 40. The chromatography column was first eluted with benzene and the fraction thus obtained was removed, after which 0.5 g of the desired product, melting (with decomposition) above 260° C., was obtained from the fraction eluted with a 10:0.5 by volume mixture of ethyl acetate and methanol.

Infrared Absorption Spectrum (Nujol mull) $\nu_{max}$ cm$^{-1}$: 3250, 1695.

Silica gel thin layer chromatography: Rf value=0.5 (Developing solvent, ethyl acetate:methanol=9:1 by volume).

Mass spectrum (m/e): 316 (M+).

EXAMPLE 55

5-t-Butyldimethylsilyloxy-4,6,7-trimethyl-2-phenyl-1,3-benzoxathiole 2.6 g of 5-hydroxy-4,6,7-trimethyl-2-phenyl-1,3-benzoxathiole, 1.3 g of imidazole and 2.9 g of t-butyldimethylsilyl chloride were dissolved in 20 ml of dimethylformamide, and the mixture was reacted for 24 hours at room temperature. At the end of this time, the reaction mixture was poured into water. The separated product was extracted with benzene, and the extract was washed with a 5% w/v aqueous solution of ammonia and then with water and dried over anhydrous sodium sulfate. The solvent was evaporated off and the product thus obtained was purified by silica gel column chromatography. From the fraction eluted with a 10:1 by volume mixture of cyclohexane and benzene were obtained 3.1 g of the title compound, melting at 95°–98° C.

EXAMPLE 56

5-t-Butyldimethylsilyloxy-2,4,6,7-tetramethyl-2-phenyl-1,3-benzoxathiole and
2-butyl-5-t-butyldimethylsilyloxy-4,6,7-trimethyl-2-phenyl-1,3-benzoxathiole 3.1 g of 5-t-butyldimethylsilyloxy-4,6,7-trimethyl-2-phenyl-1,3-benzoxathiole were dissolved in 30 ml of dry tetrahydrofuran, and 10 ml of a hexane solution containing 15% w/v of butyllithium were added dropwise at −60° C. After the dropwise addition of this reagent, the mixture was stirred for 3 hours at from −55° to −60° C., and then 4.4 g of methyl iodide were added dropwise to the solution at −60° C. After this dropwise addition, the mixture was stirred for 2 hours at −60° C. The reaction mixture was then poured into water and the product was taken up in benzene. The benzene phase was separated, washed with water and dried over anhydrous sodium sulfate. The solvent was evaporated off and the crude oil thus obtained was separated by chromatography through a silica gel Lobar column. From the first fraction eluted with a 10:1 by volume mixture of hexane and methylene chloride was obtained 1.3 g of the 2-butyl compound and, from the next fraction, were obtained 1.7 g of the 2-methyl compound.

2-methyl compound

Silica gel thin layer chromatography: Rf value=0.60 (Developing solvent, cyclohexane:benzene=4:1 by volume).

Mass spectrum (m/e): 400 (M+).

2-butyl compound

Silica gel thin layer chromatography: Rf value=0.65 (Developing solvent, cyclohexane:benzene=4:1 by volume).

Mass spectrum (m/e): 442 (M+).

EXAMPLE 57

2-Butyl-5-t-butyldimethylsilyloxy-4,6,7-trimethyl-2-phenyl-1,3-benzoxathiole

The procedures for reaction, treatment and purification of the reaction mixture described in Example 56 were repeated, but using 4.3 g of butyl bromide instead of methyl iodide, to give 2.1 g of the title compound, whose properties were the same as those of the product obtained as described in Example 56.

EXAMPLE 58

2-Allyl-5-t-butyldimethylsilyloxy-4,6,7-trimethyl-2-phenyl-1,3-benzoxathiole 4.0 g of 5-t-butyldimethylsilyloxy-4,6,7-trimethyl-2-phenyl-1,3-benzoxathiole were dissolved in 40 ml of dried tetrahydrofuran, and then 9.7 ml of a 15% w/v solution of butyllithium in hexane was added dropwise at −60° C. The mixture was then stirred at a temperature of from −55° C. to −60° C. for 2 hours, after which 2.6 ml of allyl bromide were added dropwise. After the dropwise addition, the mixture was stirred at −50° C. for 2 hours, and then subjected to the same treatment and purification as described in Example 56. 1.7 g of the corresponding 2-butyl compound was obtained from the first fractions eluted with a 20:0.5 by volume mixture of hexane and methylene chloride from a silica gel chromatography column, and then 2.9 g of the title compound were obtained from the subsequent eluate.

Silica gel thin layer chromotography: RF value=0.46 (Developing solvent, cyclohexane:benzene=4:1 by volume).

Mass spectrum (m/e): 426 (M+).

EXAMPLE 59

5-Hydroxy-2,4,6,7-tetramethyl-2-phenyl-1,3-benzoxathiole 3.0 g of 5-t-butyldimethylsilyloxy-2,4,6,7-tetramethyl-2-phenyl-1,3-benzoxathiole were dissolved in 30 ml of tetrahydrofuran. Under a stream of nitrogen, 4.5 g of acetic acid and 12.9 g of tetrabutylammonium fluoride trihydrate were then added to the mixture. The reaction mixture was then allowed to react for 2 hours at room temperature. At the end of this time, the reaction mixture was poured into water, and the resulting precipitate was extracted with benzene. The extract was washed with water and then dried over anhydrous sodium sulfate. The solvent was then distilled off. The resulting crude oily substance was subjected to silica gel column chromatography. The title compound was obtained from the portion eluted with a 1.1 by volume mixture of cyclohexane and benzene. It melted at 80°-81° C.

Infrared Absorption Spectrum (Nujol mull) $\nu_{max}$ cm$^{-1}$: 3350–3400 (broad absorption band).

Mass spectrum (m/e): 286 (M+).

EXAMPLE 60

2-Butyl-5-hydroxy-4,6,7-trimethyl-2-phenyl-1,3-benzoxathiole

2-Butyl-5-t-butyldimethylsilyloxy-4,6,7-trimethyl-2-phenyl-1,3-benzoxathiole was subjected to the same reaction, subsequent treatment and purification as described in Example 59, to yield the title compound.

Silica gel thin layer chromatography: Rf value=0.44 (Developing solvent, benzene).

Infrared Absorption Spectrum (liquid film) $\nu_{max}$ cm$^{-1}$: 3450–3550 (broad absorption band) and 3600 (sharp absorption band).

Mass spectrum (m/e): 328 (M+).

EXAMPLE 61

2-Allyl-5-hydroxy-4,6,7-trimethyl-2-phenyl-1,3-benzoxathiole

2-Allyl-5-t-butyldimethylsilyloxy-4,6,7-trimethyl-2-phenyl-1,3-benzoxathiole was subjected to the same reaction, subsequent treatment and purification as described in Example 59, to give the title compound.

Silica gel thin layer chromatography: Rf value=0.57 (Developing solvent, benzene:ethyl acetate=10:0.5 by volume).

Infrared Absorption Spectrum (liquid film) $\nu_{max}$ cm$^{-1}$: 3600, 1640.

Mass spectrum (m/e): 312 (M+).

EXAMPLE 62

5-Hydroxy-2,2,4,6,7-pentamethyl-1,3-benzoxathiole

A mixture of 4.8 g of 2-mercapto-3,5,6-trimethylhydroquinone, 1 g of p-toluenesulfonic acid, 10 g of molecular sieve 4A and 100 ml of acetone was heated under reflux for 5 hours under a stream of nitrogen. At the end of this time, the acetone was distilled off, and an aqueous solution of sodium bicarbonate was added to the residue. This mixture was extracted with ethyl acetate. The extract was washed with water and dried over anhydrous magnesium sulfate. The solvent was distilled from the extract. Benzene was added to the resulting residue. Substances which were not soluble in benzene were filtered off, and crystals precipitating from the benzene solution were removed. The portion which was readily soluble in benzene was separated by silica gel column chromatography. The portion eluted with benzene was recrystallized from petroleum ether to yield 0.1 g of the title compound, melting at 62°-64.5° C.

Mass spectrum (m/e): 224 (M+).

EXAMPLE 63

5-(1-Ethoxyethoxy)-4,6,7-trimethyl-1,3-benzoxathiole

A mixture of 7.35 g of 5-hydroxy-4,6,7-trimethyl-1,3-benzoxathiole-2-one, 20 ml of ethyl vinyl ether and 20 ml of methylene dibromide was cooled down to −20° C. under a stream of nitrogen, and then 20 mg of methanesulfonic acid were added dropwise, while stirring. After completion of the dropwise addition, the reaction temperature was gradually raised to room temperature, and the mixture was stirred for 3 hours at room temperature. To this reaction mixture were added 30 ml of water, 8.8 g of sodium bicarbonate and 1.0 g of Aliquat 336 (a trade mark for methyltrioctylammonium chloride), and the mixture was heated under reflux for 9 hours, which caused the excess methylene dibromide to vaporize gradually and leave a crude oil. This crude oil was extracted with diethyl ether, and the extract was dried over anhydrous sodium sulfate. The ether was then distilled off, to yield 12 g of an oily substance, which was purified by silica gel column chromatography. From the portion which could be eluted with a 20:1 by volume mixture of petroleum ether and diethyl ether were obtained 5.2 g of the title compound melting at 52°–54° C.

Infrared Absorption Spectrum (Nujol mull): No absorption arising from the hydroxy group or the carbonyl group of the starting material or intermediate was observed.

EXAMPLE 64

5-Hydroxy-4,6,7-trimethyl-1,3-benzoxathiole 5.0 g of 5-(1-ethoxyethoxy)-4,6,7-trimethyl-1,3-benzoxathiole (prepared as described in Example 63) were dissolved in 20 ml of methylene chloride, and 10 g of silica gel-60 (a product of Merck & Co., Inc.) and 1 ml of a 10% w/v aqueous solution of oxalic acid were added. The mixture was then reacted for 1.5 hours at room temperature, after which the silica gel was filtered off. The methylene chloride was then distilled from the solution to yield a crude product, which was extracted with benzene. The extract was dried over anhydrous sodium sulfate, and the benzene was distilled off to yield crude crystals, which were recrystallized from an approximately 10:1 by volume mixture of benzene and petroleum ether, to yield 2.8 g of the title compound, melting at 131°–132° C.

Infrared Absorption Spectrum (Nujol mull) $\nu_{max}$ cm$^{-1}$: 3330.

EXAMPLE 65

5-Benzoyloxy-2,4,6,7-tetramethyl-1,3-benzoxathiole

A mixture of 2.0 g of 5-hydroxy-2,4,6,7-tetramethyl-1,3-benzoxathiole (prepared as described in Example 40), 1.2 g of benzoyl chloride and 5 ml of pyridine was reacted for 24 hours at room temperature, and was then subjected to the same subsequent treatment and purification as described in Example 4, to give 1.8 g of the title compound, melting at 100°–102° C.

EXAMPLE 66

5-p-Methoxycarbonylbenzoyloxy-2,4,6,7-tetramethyl-1,3-benzoxathiole

The procedures for reaction, subsequent treatment and purification described in Example 65 were repeated, except that p-methoxycarbonylbenzoyl chloride was used in lieu of benzoyl chloride, to give the title compound, melting at 141°–142° C.

EXAMPLE 67

5-o-Acetoxybenzoyloxy-2,4,6,7-tetramethyl-1,3-benzoxathiole

The procedures for reaction, subsequent treatment and purification described in Example 65 were repeated, except that o-acetoxybenzoyl chloride was used in lieu of benzoyl chloride, to give the title compound.

Silica gel thin layer chromatography: Rf value=0.10 (Developing solvent, benzene:hexane=3:2 by volume).

Infrared Absorption Spectrum (liquid film) $v_{max}$ cm$^{-1}$: 1740, 1770.

Mass spectrum (m/e): 372 (M+).

EXAMPLE 68

5-(3-Methoxycarbonylpropionyloxy)-2,4,6,7-tetramethyl-1,3-benzoxathiole

The procedures for reaction, subsequent treatment and purification described in Example 65 were repeated, except that 3-methoxycarbonylpropionyl chloride was used in lieu of benzoyl chloride, to give the title compound, melting at 73°–75° C.

Infrared Absorption Spectrum (Nujol mull) $v_{max}$ cm$^{-1}$: 1730, 1745.

Mass spectrum (m/e): 324 (M+).

EXAMPLE 69

Methyl 3-(5-hydroxy-4,6,7-trimethyl-1,3-benzoxathiole-2-yl)propionate 4.2 g of methyl 3-[5-(3-methoxycarbonylpropionyloxy)-4,6,7-trimethyl-1,3-benzoxathiole-2-yl]propionate (prepared as described in Example 31) were added to a mixture of 50 ml of methanol and 14 g of 28% w/v aqueous ammonia, and the mixture was reacted for 20 hours at room temperature. The volatile matter was then evaporated from the reaction mixture under reduced pressure, and ethyl acetate was added to the residue. The ethyl acetate solution was washed with water and dried over anhydrous sodium sulfate. The ethyl acetate was then distilled off under reduced pressure. The resulting residue was subjected to silica gel column chromatography, and the desired compound was obtained from the fraction eluted with a 20:1 by volume mixture of benzene and ethyl acetate.

Silica gel thin layer chromatography: Rf value=0.55 (Developing solvent, benzene:ethyl acetate=10:1 by volume).

Mass spectrum (m/e): 282 (M+).

EXAMPLE 70

3-(5-Hydroxy-4,6,7-trimethyl-1,3-benzoxathiole-2-yl)propionamide 4.9 g of methyl 3-[5-(3-methoxycarbonylpropionyloxy)-4,6,7-trimethyl-1,3-benzoxathiole-2-yl]propionate (prepared as described in Example 31) was dissolved in 60 ml of methanol, and 17 g of 28% w/v aqueous ammonia was added to the solution. The reaction mixture was then allowed to react for 5 days at room temperature. At the end of this time, the solvent was distilled off under reduced pressure, and the residue was dissolved in ethyl acetate. The resulting solution was washed with water and dried over anhydrous sodium sulfate. The solvent was then distilled off under reduced pressure. The resulting crude product was subjected to silica gel column chromatography, and the title compound, melting at 160°–161° C., was obtained from the fraction eluted with a 3:7 by volume mixture of benzene and ethyl acetate.

Mass spectrum (m/e): 267 (M+).

EXAMPLE 71

3-(5-Hydroxy-4,6,7-trimethyl-1,3-benzoxathiole-2-yl)propanol (a) 10 g of lithium aluminum hydride were suspended in 500 ml of dried tetrahydrofuran, and then a solution of 32.0 g of methyl 3-[5-(3-methoxycarbonylpropionyloxy)-4,6,7-trimethyl-1,3-benzoxathiole-2-yl]propionate (prepared as described in Example 31) in 160 ml of tetrahydrofuran was added dropwise with stirring and ice-cooling and under a nitrogen stream to the suspension. After the dropwise addition, the reaction mixture was stirred for 1 hour at room temperature and then refluxed for 4 hours. The reaction mixture was then cooled with ice-water, after which a mixture of 10 g of ethyl acetate and 50 ml of tetrahydrofuran was added dropwise, and the mixture was stirred for 1 hour at room temperature, after which aqueous tetrahydrofuran was added dropwise. The reaction mixture was then poured into ice-water. The pH of the mixture was adjusted to an acid value by the addition of a 10% w/v aqueous solution of hydrochloric acid, and the precipitating product was extracted with ethyl acetate. The extract was washed with water and dried over anhydrous sodium sulfate. The solvent was distilled off under reduced pressure. The resulting crude product was subjected to silica gel column chromatography and the title compound, melting at 116.5°–117° C., was obtained from the fraction eluted with a 9:1 by volume mixture of benzene and ethyl acetate.

Infrared Absorption Spectrum (Nujol mull) $v_{max}$ cm$^{-1}$: 3360, 3100.

Mass spectrum (m/e): 254 (M+).

(b) Ethyl 3-[5-(3-ethoxycarbonylpropionyloxy)-4,6,7-trimethyl-1,3-benzoxathiole-2-yl)propionate (prepared as described in Example 32) was used in the same process as described in (a) above, to give the title compound, whose melting point, infrared absorption spectrum and mass spectrum were the same as those of the product described in (a) above.

(c) Butyl 3-[5-(3-butoxycarbonylpropionyloxy)-4,6,7-trimethyl-1,3-benzoxathiole-2-yl)propionate (prepared as described in Example 33) was used in the same reaction process as described in (a) above, to give the title compound, whose melting point, infrared absorption spectrum and mass spectrum were the same as those of the product described in (a) above.

EXAMPLE 72

5-Acetoxy-2-(3-acetoxypropyl)-4,6,7-trimethyl-1,3-benzoxathiole

A mixture of 1.0 g of 3-(5-hydroxy-4,6,7-trimethyl-1,3-benzoxathiole-2-yl)propanol (prepared as described in Example 71), 1.6 g of acetic anhydride and 10 ml of pyridine was reacted for 24 hours at room temperature, and the reaction mixture was then subjected to the same treatment and purification as described in Example 4, to give the title compound, melting at 78°–79° C.

Infrared Absorption Spectrum (Nujol mull) $v_{max}$ cm$^{-1}$: 1738, 1750.

Mass spectrum (m/e): 338 (M+).

EXAMPLE 73

5-Benzoyloxy-2-(3-benzoyloxypropyl)-4,6,7-trimethyl-1,3-benzoxathiole

The procedures for reaction, treatment and purification described in Example 72 were repeated, except that benzoyl chloride was used in lieu of acetic anhydride, to give the title compound melting at 114°–116° C.

Infrared Absorption Spectrum (Nujol mull) $\nu_{max}$ cm$^{-1}$: 1720, 1738.

Mass spectrum (m/e): 462 (M+).

EXAMPLE 74

5-Hydroxy-2-(3-iodopropyl)-4,6,7-trimethyl-1,3-benzoxathiole (a) 3.0 g of 3-(5-hydroxy-4,6,7-trimethyl-1,3-benzoxathiole-2-yl)propanol (prepared as described in Example 71) were dissolved in a mixture of 40 ml of benzene and 4 ml of pyridine, after which 6.2 g of triphenylphosphine were dissolved in the mixture. After the dissolution, 6.0 g of iodine was added to the solution all at once. The reaction temperature of the mixture rose to 45° C. The reaction was allowed to continue for another 30 minutes at room temperature, and then the reaction mixture was poured into water and extracted with benzene. The extract was washed with water and dried over anhydrous sodium sulfate. The solvent was then distilled off under reduced pressure. The resulting crude reaction product was subjected to silica gel Lobar column chromatography, and the title compound, melting at 72°–75° C. was obtained from the fraction eluted with benzene.

Silica gel thin layer chromatography: Rf value=0.39 (Developing solvent, cyclohexane:benzene=1:4 by volume).

Mass spectrum (m/e): 364 (M+).

(b) 2 ml of methyl iodide were added to 0.67 g of triphenyl phosphite, and then the temperature of the reaction mixture was raised to reflux temperature, after which the reaction was continued for 1 hour at a bath temperature of 100° C. The temperature of the reaction mixture was reduced to room temperature, and then 0.5 g of 3-(5-hydroxy-4,6,7-trimethyl-1,3-benzoxathiole-2-yl)propanol (prepared as described in Example 71), 1 ml of methyl iodide and 0.5 ml of dimethylformamide were added to the reaction mixture. The reaction was continued for 3 days at room temperature. At the end of this time, the title compound, having the same properties as the product of (a) above, was obtained by the same treatment and separation procedures as in (a).

(c) 120 mg of 2-(3-chloropropyl)-5-hydroxy-4,6,7-trimethyl-1,3-benzoxathiole (prepared as described in Example 77) were dissolved in 2 ml of acetone, after which 660 mg of sodium iodide were added, and the reaction mixture was heated under reflux for 10 hours. The reaction mixture was cooled and then poured into water, and the resulting precipitate was extracted with ethyl acetate. The extract was washed with water and dried over anhydrous sodium sulfate. The ethyl acetate was distilled off under reduced pressure and the resulting crude product was purified in the same manner as described in (a), to give the title compound having the same Rf value and mass spectrum as the product of (a) above.

EXAMPLE 75

5-Formyloxy-2-(3-iodopropyl)-4,6,7-trimethyl-1,3-benzoxathiole and
5-hydroxy-2-(3-iodopropyl)-4,6,7-trimethyl-1,3-benzoxathiole 1.5 g of triphenylphosphine and 1.5 g of iodine were dissolved in 5 ml of dimethylformamide, and the solution was stirred for 30 minutes at room temperature, after which 0.5 g of 3-(5-hydroxy-4,6,7-trimethyl-1,3-benzoxathiole-2-yl)propanol (prepared as described in Example 71) was added, and the reaction mixture was allowed to react for 20 hours at room temperature. The reaction mixture was then poured into water and extracted with benzene. The extract was washed with water and dried over anhydrous sodium sulfate, and the benzene was distilled off under reduced pressure. The resulting crude product was subjected to silica gel column chromatography and the final reaction products were fractionated using a 1:2 by volume mixture of cyclohexane and benzene. The desired 5-formyloxy-2-(3-iodopropyl)-4,6,7-trimethyl-1,3-benzoxathiole, melting at 91°–93° C., was obtained from the fraction first eluted.

Mass spectrum (m/e): 392 (M+).

From the fraction subsequently eluted was obtained 5-hydroxy-2-(3-iodopropyl)-4,6,7-trimethyl-1,3-benzoxathiole having the same melting point, Rf value and mass spectrum as the product of Example 74.

EXAMPLE 76

2-(3-Bromopropyl)-5-hydroxy-4,6,7-trimethyl-1,3-benzoxathiole and
2-(3-bromopropyl)-5-formyloxy-4,6,7-trimethyl-1,3-benzoxathiole 1.5 g of triphenylphosphine was dissolved in 3 ml of dimethylformamide, and then a solution of 0.9 of bromine in 2 ml of dimethylformamide was added dropwise. The mixture was allowed to react for 30 minutes at room temperature, after which 0.5 g of 3-(5-hydroxy-4,6,7-trimethyl-1,3-benzoxathiole-2-yl)propanol (prepared as described in Example 71) was added. The reaction mixture was allowed to react for a further 20 hours at room temperature. The same treatment and separation procedures as described in Example 75 were carried out. From the fraction eluted first was obtained 2-(3-bromopropyl)-5-formyloxy-4,6,7-trimethyl-1,3-benzoxathiole.

Silica gel thin layer chromatography: Rf value=0.55 (Developing solvent, cyclohexane:benzene=1:4 by volume).

Mass spectrum (m/e): 344 (M+).

From the fraction subsequently eluted was obtained 2-(3-bromopropyl)-5-hydroxy-4,6,7-trimethyl-1,3-benzoxathiole.

Silica gel thin layer chromatography: Rf value=0.36 (Developing solvent, cyclohexane:benzene=1:4 by volume).

Mass spectrum (m/e): 316 (M+).

EXAMPLE 77

2-(3-Chloropropyl)-5-hydroxy-4,6,7-trimethyl-1,3-benzoxathiole and 2-(3-chloropropyl)-4,6,7-trimethyl-5-(p-tosyloxy)-1,3-benzoxathiole 500 mg of 3-(5-hydroxy-4,6,7-trimethyl-1,3-benzoxathiole-2-yl)propanol (prepared as described in Example 71) were dissolved in 5 ml of pyridine, and then 0.41 g of p-tosyl chloride was added, whilst ice cooling. The reaction mixture was allowed to react for 20 hours at room temperature, after which it was poured into water and extracted with ethyl acetate. The extract was washed with water and dried over anhydrous sodium sulfate. The ethyl acetate was distilled off under reduced pressure, and the resulting residue was separated and purified by silica gel Lobar column chromatography.

From the fraction initially eluted with a 4:1 by volume mixture of benzene and cyclohexane was obtained the desired 2-(3-chloropropyl)-4,6,7-trimethyl-5-(p-tosyloxy)-1,3-benzoxathiole.

Silica gel thin layer chromatography: Rf value=0.70 (Developing solvent, benzene).

Mass spectrum (m/e): 426 (M+).

From the fraction eluted subsequently was obtained 2-(3-chloropropyl)-5-hydroxy-4,6,7-trimethyl-1,3-benzoxathiole.

Silica gel thin layer chromatography: Rf value=0.42 (Developing solvent, benzene).

Mass spectrum (m/e): 272 (M+).

EXAMPLE 78

5-t-Butyldimethylsilyloxy-2-(3-chloropropyl)-4,6,7-trimethyl-1,3-benzoxathiole 2.6 g of 5-hydroxy-2-(3-iodopropyl)-4,6,7-trimethyl-1,3-benzoxathiole (prepared as described in Examples 74 and 75), 0.53 g of imidazole and 1.2 g of t-butyldimethylsilyl chloride were dissolved in 25 ml of dimethylformamide, and the reaction mixture was allowed to react for 20 hours at room temperature. The reaction mixture was then poured into water and extracted with benzene. The benzene extract was separated, washed with water and dried over anhydrous sodium sulfate. The benzene was then distilled off under reduced pressure. The resulting residue was subjected to silica gel Lobar column chromatography. The title compound was obtained from the fraction eluted with a 9:1 by volume mixture of cyclohexane and benzene.

Silica gel thin layer chromatography: Rf value=0.46 (Developing solvent, cyclohexane:benzene=4:1 by volume).

Mass spectrum (m/e): 386 (M+).

EXAMPLE 79

5-t-Butyldimethylsilyloxy-2-(3-iodopropyl)-4,6,7-trimethyl-1,3-benzoxathiole (a) 5.2 g of t-butyldimethylsilyl chloride and 4.6 g of imidazole were dissolved in 80 ml of benzene, and then the reaction mixture was heated for 1 hour at 50° C., after which a solution of 6.3 g of 5-hydroxy-2-(3-iodopropyl)-4,6,7-trimethyl-1,3-benzoxathiole (prepared as described in Examples 74 and 75) in 10 ml of benzene was added and the reaction mixture was allowed to react for 8 hours at 40°-45° C. The reaction product was cooled, poured into water, and then extracted with benzene. The extract was washed with water and then dried over anhydrous sodium sulfate. The solvent was distilled off under reduced pressure. The resulting residue was subjected to silica gel column chromatography and the title compound was obtained from the fraction eluted with a 9:1 by volume mixture of cyclohexane and benzene.

Silica gel thin layer chromatography: Rf value=0.39 (Developing solvent, cyclohexane:benzene=9:1 by volume).

Infrared Absorption Spectrum (liquid film): no absorption attributable to a hydroxy group was observed.

Mass spectrum (m/e): 478 (M+).

(b) A mixture of 1.06 g of 5-t-butyldimethylsilyloxy-2-(3-chloropropyl)-4,6,7-trimethyl-1,3-benzoxathiole (prepared as described in Example 78), 4.1 g of sodium iodide and 40 ml of acetone was heated under reflux for 10 hours. The reaction product was then cooled, after which it was treated in the same manner as described in (a) above, to give the title compound having the same Rf value, infrared absorption spectrum and mass spectrum as the product of (a) above.

EXAMPLE 80

5-(5-t-Butyldimethylsilyloxy-4,6,7-trimethyl-1,3-benzoxathiole-2-yl)-2,2-dimethylpentanoic acid 2.4 g of diisopropylamine were dissolved in 60 ml of tetrahydrofuran, and then 1.2 g of a 50% w/w oily suspension of sodium hydride was added under a stream of nitrogen. Meanwhile, 2.4 g of isobutyric acid were dissolved in 5 ml of tetrahydrofuran, and this solution was then added dropwise to the first-prepared solution. After hydrogen and heat generation had ceased, the mixture was further refluxed for 30 minutes, and then cooled down to 0° C.

25.4 ml of a 10% w/v solution of butyllithium in hexane was then added dropwise to the reaction mixture. After completion of the dropwise addition, the mixture was maintained at 0° C. for 30 minutes, and then stirred for 30 minutes at room temperature. The reaction mixture was again cooled down to 0° C., after which a solution of 6.5 g of 5-t-butyldimethylsilyloxy-2-(3-iodopropyl)-4,6,7-trimethyl-1,3-benzoxathiole (prepared as described in Example 79) in 10 ml of tetrahydrofuran was added dropwise. After the dropwise addition, the reaction mixture was kept at 0° C. for 30 minutes, and then its temperature was gradually raised to room temperature, at which temperature the reaction mixture was reacted for 20 hours. The reaction mixture was then poured into ice-water containing 30 ml of 10% w/v aqueous hydrochloric acid, and the mixture was extracted with benzene. The extract was washed with water and then dried over anhydrous sodium sulfate. The benzene was distilled off under reduced pressure. The resulting residue was subjected to silica gel column chromatography, and the title compound was obtained from the fraction eluted with a 100:3 by volume mixture of benzene and ethyl acetate.

Silica gel thin layer chromatography: Rf value=0.13 (Developing solvent, benzene:ethyl acetate=20:1 by volume).

Mass spectrum (m/e): 438 (M+).

EXAMPLE 81

5-(5-Hydroxy-4,6,7-trimethyl-1,3-benzoxathiole-2-yl)-2,2-dimethylpentanoic acid 3.6 g of 5-(5-t-butyldimethylsilyloxy-4,6,7-trimethyl-1,3-benzoxathiole-2-yl)-2,2-dimethylpentanoic acid (prepared as described in Example 80), 14.2 g of tetrabutylammonium fluoride trihydrate and 4.9 g of acetic acid were dissolved in 50 ml of tetrahydrofuran, and the mixture was reacted for 20 hours at room temperature. The reaction mixture was then condensed by evaporation under reduced pressure, and the residue was dissolved in ethyl acetate. The ethyl acetate solution was washed with water and dried over anhydrous sodium sulfate, after which the ethyl acetate was distilled off under reduced pressure. The resulting crude product was subjected to silica gel column chromatography. The title compound was obtained from the fraction eluted with a 9:1 by volume mixture of benzene and ethyl acetate.

Silica gel thin layer chromatography: Rf value=0.40 (Developing solvent, benzene:methanol=10:1 by volume).

Mass spectrum (m/e): 324 (M+).

EXAMPLE 82

5-(5-Hydroxy-4,6,7-trimethyl-1,3-benzoxathiole-2-yl)-2,2-dimethylpentanol 0.3 g of lithium aluminum hydride was suspended in 30 ml of tetrahydrofuran, and a solution of 1.7 g of 5-(5-hydroxy-4,6,7-trimethyl-1,3-benzoxathiole-2-yl)-2,2-dimethylpentanoic acid (prepared as described in Example 81) in 5 ml of tetrahydrofuran was added dropwise under a stream of nitrogen and with ice-cooling to the suspension. After the dropwise addition, the reaction mixture was kept at room temperature for 1 hour and was then heated under reflux for 2 hours. The reaction mixture was then poured into ice-water and extracted with ethyl acetate. The extract was washed with water and dried over anhydrous sodium sulfate, after which the ethyl acetate was distilled off under reduced pressure. The resulting residue was subjected to silica gel Lobar column chromatography, and the title compound was obtained by elution with a 9:1 by volume mixture of benzene and ethyl acetate.

Silica gel thin layer chromatography: Rf value=0.43 (Developing solvent, benzene:methanol=10:1 by volume).

Mass spectrum (m/e): 310 (M+).

EXAMPLE 83

5-Hydroxy-2-(3-methoxymethoxypropyl)-4,6,7-trimethyl-1,3-benzoxathiole 5.0 g of 3-(5-hydroxy-4,6,7-trimethyl-1,3-benzoxathiole-2-yl)propanol (prepared as described in Example 71) were dissolved in 40 ml of dimethylformamide, and 260 mg of a 55% w/w oily suspension of sodium hydride was added at room temperature. The reaction mixture was then heated for 1 hour at 40°–45° C., after which it was cooled with ice-water, and then a solution of 1.6 g of chloromethyl methyl ether in 5 ml of benzene was added dropwise. After completion of the addition, the temperature of the mixture was gradually raised and then the mixture was heated for 1 hour at 50°–55° C. The reaction mixture was then poured into water and extracted with benzene. The extract was washed with water and then dried over anhydrous sodium sulfate. The solvent was distilled off under reduced pressure. The resulting residue was subjected to silica gel Lobar column chromatography, and the title compound was obtained from the fraction eluted with a 100:3 by volume mixture of benzene and ethyl acetate.

Silica gel thin layer chromatography: Rf value=0.35 (Developing solvent, benzene:ethyl acetate=20:1 by volume).

Mass spectrum (m/e): 298 (M+).

Nuclear Magnetic Resonance Spectrum (CDCl$_3$) δ ppm:
  3.37 (3H, singlet, methoxy);
  3.60 (2H, triplet, J=6 Hz, —CH$_2$—C$\underline{H_2}$—O—);
  4.45 (1H, singlet, disappeared on adding heavy water, 5-hydroxy);
  4.65 (2H, singlet, —O—CH$_2$—O—);
  6.03 (1H, triplet, J=6 Hz, 2-H on benzoxathiole).

EXAMPLE 84

5-Acetoxy-2-(3-methoxymethoxypropyl)-4,6,7-trimethyl-1,3-benzoxathiole 100 mg of 5-hydroxy-2-(3-methoxymethoxypropyl)-4,6,7-trimethyl-1,3-benzoxathiole (prepared as described in Example 83) were dissolved in 1 ml of pyridine, and 50 mg of acetic anhydride were added. The reaction mixture was allowed to react for 20 hours at room temperature. Benzene was then added to the reaction mixture, and the benzene solution was washed with water and then dried over anhydrous sodium sulfate. The benzene was distilled off under reduced pressure. The resulting residue was subjected to silica gel column chromatography. The title compound was obtained from the fraction eluted with a 20:1 by volume mixture of benzene and ethyl acetate.

Silica gel thin layer chromatography: Rf value=0.38 (Developing solvent, benzene:ethyl acetate=20:1 by volume).

Mass spectrum (m/e): 340 (M+).

Nuclear Magnetic Resonance Spectrum (CDCl$_3$) δ ppm:
  2.32 (3H, singlet, acetyl);
  3.39 (3H, singlet, methoxy);
  3.60 (2H, triplet, J=6 Hz, —CH$_2$—C$\underline{H_2}$—O—);
  4.65 (2H, singlet, O—CH$_2$—O);
  6.11 (1H, triplet, J=6 H$\underline{z}$, 2-H of benzoxathiole).

EXAMPLE 85

3-(5-Methoxymethoxy-4,6,7-trimethyl-1,3-benzoxathiole-2-yl)propanol 340 mg of a 55% w/w oily suspension of sodium hydride was added to 20 ml of dimethylformamide, followed by 2.0 g of crystals of 3-(5-hydroxy-4,6,7-trimethyl-1,3-benzoxathiole-2-yl)propanol (prepared as described in Example 71), with ice cooling and under a stream of nitrogen. The reaction mixture was then cooled with ice for 30 minutes, after which it was allowed to react for 1 hour at room temperature; it then was again cooled with ice. A solution of 630 mg of chloromethyl methyl ether in 2 ml of benzene was then added dropwise, after which the temperature of the reaction mixture was gradually raised and the reaction mixture was allowed to react further for 20 hours at room temperature. The reaction mixture was then poured into water and extracted with benzene. The extract was washed with water and then dried over anhydrous sodium sulfate. The solvent was distilled off under reduced pressure, and the resulting residue was subjected to silica gel Lobar column chromatography. The title compound was obtained from the fraction eluted with a 9:1 by volume mixture of benzene and ethyl acetate.

Silica gel thin layer chromatography: Rf value=0.41 (Developing solvent, benzene:ethyl acetate=4:1 by volume).

Mass spectrum (m/e): 298 (M+).

Nuclear Magnetic Resonance Spectrum (CDCl$_3$) δ ppm:
1.69 (1H, singlet, disappeared on addition of heavy water);
3.60 (3H, singlet, methoxy);
3.70 (2H, triplet, J=6 Hz, —CH$_2$—CH$_2$—O—);
4.90 (2H, singlet, —O—Ch$_2$—O—);
6.09 (1H, triplet, J=6 Hz, 2-H of benzoxathiole.

EXAMPLE 86

2-(3-Iodopropyl)-5-methoxymethoxy-4,6,7-trimethyl-1,3-benzoxathiole 1.0 g of 3-(5-methoxymethoxy-4,6,7-trimethyl-1,3-benzoxathiole-2-yl)propanol (prepared as described in Example 85) was dissolved in a mixture of 15 ml of benzene and 1.5 ml of pyridine, and then 1.7 g of triphenylphosphine, followed by 1.7 g of iodine, was added to the solution. The mixture was stirred for 40 minutes at room temperature. The product was poured into water and extracted with benzene. The extract was washed with water and then dried over anhydrous sodium sulfate. The benzene was distilled off to yield a crude product, which was subjected to silica gel column chromatography. The title compound was obtained from the fraction eluted with benzene.

Silica gel thin layer chromatography: Rf value=0.59 (Developing solvent, benzene).

Mass spectrum (m/e): 408 (M+).

EXAMPLE 87

2-(3-Bromopropyl)-5-methoxymethoxy-4,6,7-trimethyl-1,3-benzoxathiole 2.6 g of 3-(5-methoxymethoxy-4,6,7-trimethyl-1,3-benzoxathiole-2-yl)propanol (prepared as described in Example 85) and 4.6 g of triphenylphosphine were dissolved in 30 ml of benzene, and 3 ml of dry pyridine were added to the solution. 4.4 g of bromine were then added dropwise at room temperature to this reaction mixture. The temperature rose as the bromine was added, and the mixture was allowed to stand until this temperature rise had finished and the mixture had returned to room temperature. The reaction mixture was then stirred for 40 minutes at room temperature, whereupon crystals formed. Water was added to the reaction mixture, which was then extracted with benzene. The extract was washed with water and then dried over anhydrous sodium sulfate. The benzene was distilled off under reduced pressure. The resulting residue was subjected to silica gel column chromatography. The title compound was obtained from the fraction eluted with a 2:3 by volume mixture of cyclohexane and benzene.

Silica gel thin layer chromatography: Rf value=0.36 (Developing solvent, cyclohexane:benzene=1:1 by volume).

Mass spectrum (m/e): 360 (M+).

EXAMPLE 88

2-[3-(2-Dimethylaminoethoxy)propyl]-5-methoxymethoxy-4,6,7-trimethyl-1,3-benzoxathiole (a) 210 mg of 2-dimethylaminoethanol were dissolved in 3 ml of dimethylformamide, and then 100 mg of a 50% w/w oily suspension of sodium hydride were added to the solution. This reaction mixture was then heated for 1 hour at 50° C. The reaction mixture was then cooled with ice, and a solution of 900 mg of 2-(3-iodopropyl)-5-methoxymethoxy-4,6,7-trimethyl-1,3-benzoxathiole (prepared as described in Example 86) in 2 ml of dimethylformamide was added dropwise, while stirring. After completion of the dropwise addition, the temperature of the reaction mixture was gradually raised, and then the mixture was heated for a further 2 hours at 50° C. The reaction mixture was then poured into water, and the resulting precipitate was extracted with benzene. The extract was washed with water and dried over anhydrous sodium sulfate. The benzene was distilled off under reduced pressure. The residual crude oily reaction product was separated by silica gel column chromatography. The fraction eluted with benzene was removed, while the fraction eluted with a 20:1 by volume mixture of ethyl acetate and triethylamine was subjected to silica gel Lobar column chromatography, eluted with the same eluent, to give the title compound.

Silica gel thin layer chromatography: Rf value=0.38 (Developing solvent, ethyl acetate:triethylamine=20:1 by volume).

Mass spectrum (m/e): 369 (M+).

(b) 740 mg of 2-dimethylaminoethanol were dissolved in 10 ml of dimethyl sulfoxide, and 220 mg of a 50% w/w oily suspension of sodium hydride was added to the resulting solution; the reaction mixture was then heated at 50° C. for 1 hour, after which it was cooled down with ice, and a solution of 1.68 g of 2-(3-bromopropyl)-5-methoxymethoxy-4,6,7-trimethyl-1,3-benzoxathiole (prepared as described in Example 87) in 5 ml of dimethyl sulfoxide was added dropwise, while stirring. The reaction product was then subjected to the same reaction process, extraction and separation procedures as described in (a) above, to give the title compound with the same Rf value and mass spectrum as those of the product obtained in (a).

EXAMPLE 89

2-Allyl-5-methoxymethoxy-4,6,7-trimethyl-1,3-benzoxathiole

In the process described in Example 88 (a) and (b), the crude oily reaction produce was subjected to silica gel column chromatography, and then the column was eluted with benzene, to give the title compound.

Silica gel thin layer chromatography: Rf value=0.60 (Developing solvent, benzene).

Mass spectrum (m/e): 280 (M+).

EXAMPLE 90

2-[3-(2-Dimethylaminoethoxy)propyl]-5-hydroxy-4,6,7-trimethyl-1,3-benzoxathiole 330 mg of 2-[3-(2-dimethylaminoethoxy)propyl]-5-methoxymethoxy-4,6,7-trimethyl-1,3-benzoxathiole (prepared as described in Example 88) were dissolved in 5 ml of acetic acid, and then 5 drops of 10% v/v aqueous sulfuric acid was added using a Komagome pipette; the mixture was then heated for 5 hours at 70°-75° C. The acetic acid solution and then condensed by evaporation under reduced pressure, and the condensate was poured into ice-water, neutralized with potassium carbonate and extracted with ethyl acetate. The ethyl acetate solution was washed with water and the dried over anhydrous sodium sulfate. The ethyl acetate was then distilled off under reduced pressure. The resulting residue was then subjected to silica gel column chromatography, and the title compound was obtained from the fraction eluted with a 20:1 by volume mixture of ethyl acetate and triethylamine.

Silica gel thin layer chromatography: Rf value=0.30 (Developing solvent, ethyl acetate:triethylamine=20:1 by volume).

Mass spectrum (m/e): 325 (M+).

EXAMPLE 91

2-Allyl-5-hydroxy-4,6,7-trimethyl-1,3-benzoxathiole 0.9 g of 2 allyl-5-methoxymethoxy-4,6,7-trimethyl-1,3-benzoxathiole (prepared as described in Example 89) was dissolved in 8 ml of acetic acid, and 3 drops of 10% v/v aqueous sulfuric acid were added to the resulting solution, which was then heated at 50° C. for 30 minutes. The solution was then cooled down to room temperature, and the reaction mixture was condensed by evaporation under reduced pressure. The condensate was dissolved in benzene, and the solution was washed with water and then dried over anhydrous sodium sulfate. The benzene was distilled off, and the resulting crude product was purified by silica gel Lobar column chromatography. The title compound, melting at 78.5°–79.5° C., was obtained from the fraction eluted with benzene.

Mass spectrum (m/e): 236 (M+).

EXAMPLE 92

5-t-Butyldimethylsilyloxy-4,6,7-trimethyl-1,3-benzoxathiole 0.84 g of 5-hydroxy-4,6,7-trimethyl-1,3-benzoxathiole (prepared as described in Example 64) was dissolved in 5 ml of dimethylformamide, and then 0.58 g of imidazole and 1.29 g of t-butyldimethylsilyl chloride were added to the resulting solution. The mixture was then stirred for 7 hours at 50° C., after which it was allowed to stand overnight at room temperature. The solvent was then distilled off under reduced pressure, and the residue was extracted with benzene. The extract was washed with a saturated aqueous solution of sodium bicarbonate and with water, and then dried over anhydrous sodium sulfate. The solvent was then distilled off. The resulting residue was subjected to column chromatography through 40 g of silica gel eluted with hexane and with mixtures of hexane and benzene ranging from 10:1 to 2:1 by volume, to yield 1.26 g of the title compound as a colorless oily substance.

Silica gel thin layer chromatography: Rf value=0.80 (Developing solvent, benzene: hexane=2:1 by volume).

EXAMPLE 93

5-t-Butyldimethylsilyloxy-4,6,7-trimethyl-1,3-benzoxathiole-3-oxide

The whole of the 5-t-butyldimethylsilyloxy-4,6,7-trimethyl-1,3-benzoxathiole obtained as described in Example 92 was dissolved in 100 ml of methylene chloride, and 0.99 g of m-chloroperbenzoic acid was added, with ice cooling, to the resulting solution. The reaction mixture was then stirred for 1 hour at the same temperature, after which it was poured into a saturated aqueous solution of sodium bicarbonate, extracted with chloroform, washed with water and dried over anhydrous sodium sulfate. The solvent was then distilled off, whereupon the residue crystallized. The crystals were washed with carbon tetrachloride, yielding 1.30 g of the title compound, melting at 100°–101° C.

Silica gel thin layer chromatography: Rf value=0.52 (Developing solvent, benzene:ethyl acetate=1:1 by volume).

Mass spectrum (m/e): 326 (M+).

EXAMPLE 94

5-Acetoxy-4,6,7-trimethyl-2-propyl-1,3-benzoxathiole

A mixture of 1.6 g of 5-hydroxy-4,6,7-trimethyl-2-propyl-1,3-benzoxathiole (prepared as described in Example 42), 0.8 g of acetic anhydride and 10 ml of pyridine was reacted at room temperature for 15 hours and the reaction mixture was then treated with purified in the same manner as described in Example 4, to give 1.8 g of the title compound as a pale yellow oily substance.

Silica gel thin layer chromatography: Rf value=0.57 (Developing solvent, benzene).

Infrared Absorption Spectrum (liquid film) $\nu_{max}$ cm$^{-1}$: 1752.

Mass spectrum (m/e): 280 (M+).

EXAMPLES 95–98

The following compounds were prepared by essentially the same procedures as described in the foregoing Examples:

EXAMPLE 95

6-t-Butyl-5-butyryloxy-2-methyl-1,3-benzoxathiole

Silica gel thin layer chromatography: Rf value=0.24 (Developing solvent, hexane:ethyl acetate=50:1 by volume).

Mass spectrum (m/e): 294 (M+).

Nuclear Magnetic Resonance Spectrum (CDCl$_3$) δ ppm:
1.03 (3H, triplet, J=7.5 Hz, —O—CO—CH$_2$—CH$_2$—C$\underline{H}_3$);
1.30 (9$\underline{H}$, singlet, t-butyl);
1.3–2.0 (2H, multiplet, —O—CO—CH$_2$—C$\underline{H}_2$—CH$_3$);
1.77 (3H, doublet, J=6 Hz, >CH—CH$_3$);
2.52 (2H, triplet, J=7.5 Hz, —O—CO—C$\underline{H}_2$—CH$_2$—CH$_3$);
6.17 (1H, quartet, J=6 Hz, 2-H on benzoxathiole);
6.76 (1H, singlet, 4-H on benzoxathiole);
6.83 (1H, singlet, 7-H on benzoxathiole).

EXAMPLE 96

6-t-Butyl-5-butyryloxy-2-propyl-1,3-benzoxathiole

Silica gel thin layer chromatography: Rf value=0.36 (Developing solvent, hexane:ethyl acetate=50:1 by volume).

Mass spectrum (m/e): 322 (M+).

Nuclear Magnetic Resonance Spectrum (CDCl$_3$) δ ppm:
1.30 (9H, singlet, t-butyl);
6.07 (1H, triplet, J=6 Hz, 2-H on benzoxathiole);
6.76 (1H, singlet, 4-H on benzoxathiole); 6.82 (1H, singlet, 7-H on benzoxathiole).

EXAMPLE 97

6-t-Butyl-5-hydroxy-2-propyl-1,3-benzoxathiole

Silica gel thin layer chromatography: Rf value=0.54 (Developing solvent, benzene).

Mass spectrum (m/e): 252 (M+).

Nuclear Magnetic Resonance Spectrum (CDCl$_3$) δ ppm:
0.97 (3H, triplet, J=7 Hz, —CH$_2$CH$_2$C$\underline{H}_3$);

1.3-1.7 (2H, multiplet, —CH$_2$CH$_2$CH$_3$);
1.36 (9H, singlet, t-butyl);
1.98 (2H, doublet of triplets, J=6 & 12 Hz, —CH$_2$CH$_2$CH$_3$);
4.74 (1H, singlet, 5-hydroxy);
6.02 (1H, triplet, J=6 Hz, 2-H on benzoxathiole);
6.49 (1H, singlet, 4-H on benzoxathiole);
6.77 (1H, singlet, 7-H on benzoxathiole).

EXAMPLE 98

6-t-Butyl-5-hydroxy-2-methyl-1,3-benzoxathiole

Silica gel thin layer chromatography: Rf value=0.46 (Developing solvent, benzene).

Mass spectrum (m/e): 224 (M+).

Nuclear Magnetic Resonance Spectrum (CDCl$_3$) δppm:
1.37 (9H, singlet, t-butyl);
1.77 (3H, doublet, J=6 Hz, 2-methyl);
4.47 (1H, singlet, 5-hydroxy);
6.13 (1H, quartet, J=6 Hz, 2-H on benzoxathiole);
6.50 (1H, singlet, 4-H on benzoxathiole);
6.77 (1H, singlet, 7-H on benzoxathiole).

By following essentially the same procedures as described in the foregoing Examples, it was possible to obtain the following compounds:
5-Benzoyloxy-4,6,7-trimethyl-2-propyl-1,3-benzoxathiole
5-Acetoxy-6-t-butyl-2-propyl-1,3-benzoxathiole
5-Benzoyloxy-6-t-butyl-2-propyl-1,3-benzoxathiole
5-Acetoxy-6-t-butyl-2-methyl-1,3-benzoxathiole
6-t-Butyl-5-hydroxy-1,3-benzoxathiole
6-t-Butyl-2-hexyl-5-hydroxy-1,3-benzoxathiole
6-t-Butyl-5-hydroxy-2-phenyl-1,3-benzoxathiole
3-(6-t-Butyl-5-hydroxy-1,3-benzoxathiole-2-yl)propanol
5-Acetoxy-2-(3-acetoxypropyl)-6-t-butyl-1,3-benzoxathiole
5-Benzoyloxy-2-(3-benzoyloxypropyl)-6-t-butyl-1,3-benzoxathiole

EXAMPLE 99

Inhibition of formation and release of SRS-A

The ability of compounds of the invention to inhibit the formation and release of SRS-A was investigated employing the technique of S. Watanabe-Kohno and C. W. Parker [Journal of Immunology, 125, 946 (1980)]. In these experiments, albumin was used as the antigen and was added to sensitized guinea pig (Hartley, male) lung slices 15 minutes after pre-incubation with the test compound. The amount of SRS-A formed and released under these conditions was assayed by a superfusion method, using a preparation of isolated guinea pig ileum. Other details of the technique employed are as described by Watanabe-Kohno and Parker (op. cit.).

From the results were determined the concentration of the test compound required to inhibit by 50% formation and release of SRS-A (I$_{50}$, μg/ml). The results are reported in Table 1.

TABLE 1

| Compound of Example No. | I$_{50}$ (μg/ml) (95% confidence limits) |
|---|---|
| 40 | 0.45 (0.37–0.56) |
| 42 | 0.91 (0.70–1.2) |
| 64 | 0.47 (0.31–0.72) |
| 71 | 0.37 (0.26–0.52) |
| 94 | 0.81 (0.48–1.4) |

EXAMPLE 100

Inhibition of lipid peroxide formation

This was investigated by the ferrous sulphate/cysteine method described by Malvy et al. [Biochem. Biophys. Res. Commun., 95, 734 (1980)]. The compound under test at various concentrations, cysteine (500 μM) and ferrous sulphate (5 μM) were added and allowed to react with a rat liver microsomal preparation. The amount of lipid peroxide thus formed was measured according to the thiobarbituric acid (TBA) method and the concentration of the compound under test required to inhibit the formation of lipid peroxide by 50% (I$_{50}$ μg/ml) was calculated. As can be seen from the results reported in Table 2, the compounds of the invention significantly inhibited lipid peroxide formation at very low concentrations.

TABLE 2

| Compound of Example No. | I$_{50}$ (μg/ml) |
|---|---|
| 40 | <0.1 |
| 42 | <0.1 |
| 64 | <0.1 |
| 71 | 0.1–0.3 |

We claim:
1. A compound of formula (I):

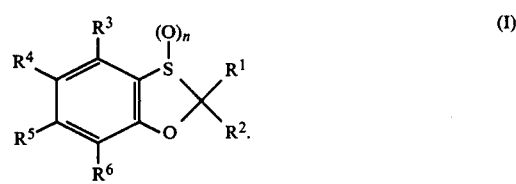

in which:
R$^1$ represents a hydrogen atom, a C$_1$–C$_{10}$ alkyl group, a substituted C$_1$–C$_{10}$ alkyl group, a C$_2$–C$_6$ alkenyl group, a C$_6$–C$_{10}$ carbocyclic aryl group, a substituted C$_6$–C$_{10}$ carbocyclic aryl group or an alkoxycarbonyl group wherein the alkoxy parts has from 1 to 6 carbon atoms, said substituents on said alkyl and aryl groups being selected from the group consisting of:
halogen atoms, hydroxy groups, C$_1$–C$_7$ aliphatic acyloxy groups, C$_6$–C$_{10}$ carbocyclic aryl carboxylic acyloxy groups, α-alkoxyalkoxy groups where both alkoxy parts have from 1 to 6 carbon atoms, a tetrahydro-2-furanyloxy- or tetrahydropyranyloxy group, trialkylsilyloxy groups where each alkyl part has from 1 to 6 carbon atoms, aralkyloxy groups where the aryl part is C$_6$–C$_{10}$ carbocyclic aryl and the alkyl part is C$_1$–C$_6$ alkyl, C$_1$–C$_6$ alkoxy groups, C$_1$–C$_6$ aminoalkoxy groups, alkylaminoalkoxy groups where the alkyl and alkoxy parts both have from 1 to 6 carbon atoms, dialkylaminoalkoxy groups where the alkyl and alkoxy parts all have from 1 to 6 carbon atoms, carboxy groups, alkoxycarbonyl groups where the alkoxy part has from 1 to 6 carbon atoms, carbamoyl groups, alkylcarbamoyl groups where the alkyl part has from 1 to 6 carbon atoms, dialkylcarbamoyl groups where both alkyl parts have from 1 to 6 carbon atoms and, as substituents on aryl groups only, C$_1$–C$_6$ alkyl groups;

$R^2$ represents a hydrogen atom, a $C_1$-$C_6$ alkyl group or a $C_3$ or $C_4$ alkyl group;

$R^3$ represents a hydrogen atom or a $C_1$-$C_6$ alkyl group;

$R^4$ represents a hydroxy group, a $C_1$-$C_{21}$ aliphatic acyloxy group or a $C_6$-$C_{10}$ carbocyclic aryl carboxylic acyloxy group;

$R^5$ represents a $C_1$-$C_{12}$ alkyl group, a $C_1$-$C_6$ alkoxy group, a hydroxy group, a $C_1$-$C_7$ aliphatic acyloxy group or a $C_6$-$C_{10}$ carbocyclic aryl carboxylic acyloxy group;

$R^6$ represents a hydrogen atom, a $C_1$-$C_6$ alkyl group or a $C_1$-$C_6$ alkoxy group; and n is 0, 1, or 2;

and pharmaceutically acceptable salts thereof.

2. A compound as claimed in claim 1, wherein:

$R^1$ represents a hydrogen atom, a $C_1$-$C_{10}$ alkyl group, a $C_1$-$C_{10}$ alkyl group having from 1 to 3 substituents selected from the group consisting of halogen atoms, hydroxy groups, alkoxycarbonyl groups wherein the alkoxy part has from 1 to 6 carbon atoms, $C_1$-$C_7$ aliphatic acyloxy groups, said aryl acyloxy groups, α-alkoxyalkoxy groups wherein both alkoxy parts have from 1 to 6 carbon atoms, said tetrahydro-2-furanyloxy- or tetrahydropyronyloxy groups, trialkylsilyloxy groups wherein each alkyl part has from 1 to 6 carbon atoms, aralkyloxy groups wherein the aryl part is $C_6$-$C_{10}$ carbocyclic aryl and the alkyl part is $C_1$-$C_6$ alkyl and carboxy groups, a $C_2$-$C_6$ alkenyl group, a phenyl group or a phenyl group having from 1 to 3 substituents selected from the group consisting of $C_1$-$C_6$ alkyl groups, halogen atoms, hydroxy groups, $C_1$-$C_7$ aliphatic acyloxy groups, said aryl acyloxy groups, α-alkoxyalkoxy groups where each alkoxy part has from 1 to 6 carbon atoms, said tetrahydro-2-furanyloxy- or tetrahydro-pyranyloxy-groups, trialkylsilyloxy groups where each alkyl part has from 1 to 6 carbon atoms and aralkyloxy groups where the aryl part is $C_6$-$C_{10}$ carbocyclic aryl and the alkyl part is $C_1$-$C_6$ alkyl; and $R^2$ represents a hydrogen atom.

3. A compound as claimed in claim 1, wherein:

$R^3$ represents a hydrogen atom or a $C_1$-$C_6$ alkyl group; $R^5$ represents a $C_1$-$C_6$ alkyl group; and $R^6$ represents a hydrogen atom or a $C_1$-$C_6$ alkyl group.

4. A compound as claimed in claim 3, wherein n is 0.

5. A compound as claimed in claim 1, wherein n is 0.

6. A compound as claimed in claim 1, wherein:

$R^1$ represents a hydrogen atom, a $C_1$-$C_6$ alkyl group, a $C_1$-$C_6$ alkyl group having from 1 to 3 substituents selected from the group consisting of hydroxy groups, $C_1$-$C_7$ aliphatic acyloxy groups and benzoyloxy groups, a phenyl group, or a phenyl group having from 1 to 3 substituents selected from the group consisting of hydroxy groups and $C_1$-$C_7$ aliphatic acyloxy groups; $R^2$ represents a hydrogen atom; $R^3$ represents a $C_1$-$C_6$ alkyl group; $R^4$ represents a hydroxy group, a $C_1$-$C_7$ aliphatic acyloxy group or a benzoyloxy group; $R^5$ represents a $C_1$-$C_6$ alkyl group; $R^6$ represents a $C_1$-$C_6$ alkyl group; and n is 0.

7. 5-Acetoxy-2,4,6,7-tetramethyl-1,3-benzoxathiole as claimed in claim 1.

8. 5-Hydroxy-2,4,6,7-tetramethyl-1,3-benzoxathiole as claimed in claim 1.

9. 2-Ethyl-5-hydroxy-4,6,7-trimethyl-1,3-benzoxathiole as claimed in claim 1.

10. 5-Hydroxy-4,6,7-trimethyl-2-propyl-1,3-benzoxathiole as claimed in claim 1.

11. 5-Hydroxy-2-isopropyl-4,6,7-trimethyl-1,3-benzoxathiole as claimed in claim 1.

12. 2-Butyl-5-hydroxy-4,6,7-trimethyl-1,3-benzoxathiole as claimed in claim 1.

13. 2-Hexyl-5-hydroxy-4,6,7-trimethyl-1,3-benzoxathiole as claimed in claim 1.

14. 3-(5-Hydroxy-4,6,7-trimethyl-1,3-benzoxathiole-2-yl)propionic acid as claimed in claim 1.

15. 5-Hydroxy-4,6,7-trimethyl-2-phenyl-1,3-benzoxathiole as claimed in claim 1.

16. 5-Hydroxy-2-(o-hydroxyphenyl)-4,6,7-trimethyl-1,3-benzoxathiole as claimed in claim 1.

17. 5-Hydroxy-4,6,7-trimethyl-1,3-benzoxathiole as claimed in claim 1.

18. 5-Benzoyloxy-2,4,6,7-tetramethyl-1,3-benzoxathiole as claimed in claim 1.

19. Methyl 3-(5-hydroxy-4,6,7-trimethyl-1,3-benzoxathiole-2-yl)propionate as claimed in claim 1.

20. 3-(5-Hydroxy-4,6,7-trimethyl-1,3-benzoxathiole-2-yl)propanol as claimed in claim 1.

21. 2-Allyl-5-hydroxy-4,6,7-trimethyl-1,3-benzoxathiole as claimed in claim 1.

22. 5-Acetoxy-4,6,7-trimethyl-2-propyl-1,3-benzoxathiole as claimed in claim 1.

23. 5-Benzoyloxy-4,6,7-trimethyl-2-propyl-1,3-benzoxathiole as claimed in claim 1.

24. 6-t-Butyl-5-hydroxy-2-propyl-1,3-benzoxathiole as claimed in claim 1.

25. 5-Acetoxy-6-t-butyl-2-propyl-1,3-benzoxathiole as claimed in claim 1.

26. 6-t-Butyl-5-hydroxy-2-methyl-1,3-benzoxathiole as claimed an claim 1.

27. 5-Acetoxy-6-t-butyl-2-methyl-1,3-benzoxathiole as claimed in claim 1.

28. 6-t-Butyl-5-butyryloxy-2-methyl-1,3-benzoxathiole as claimed in claim 1.

29. 3-(6-t-Butyl-5-hydroxy-1,3-benzoxathiole-2-yl)propanol as claimed in claim 1.

* * * * *